United States Patent [19]

Rorer

[11] Patent Number: 4,494,979
[45] Date of Patent: Jan. 22, 1985

[54] BENZOFURAN SULFAMATES

[75] Inventor: Morris P. Rorer, Newark, Del.

[73] Assignee: E. I. Du Pont de Nemours and Company, Wilmington, Del.

[21] Appl. No.: 387,951

[22] Filed: Jun. 15, 1982

Related U.S. Application Data

[63] Continuation-in-part of Ser. No. 286,602, Jul. 24, 1981, abandoned.

[51] Int. Cl.$^3$ .................. C07D 405/12; C07D 409/12; A01N 43/54; A01N 43/66
[52] U.S. Cl. ............................................. 71/92; 71/73; 544/209; 544/212; 544/323; 544/324; 544/321; 544/331; 544/332
[58] Field of Search ............... 544/320, 321, 331, 332, 544/323, 324; 71/92

[56] References Cited

U.S. PATENT DOCUMENTS 4,032,649  6/1977  Singerman .......................... 424/275
4,191,553  3/1980  Reap ....................................... 71/92

FOREIGN PATENT DOCUMENTS 646171  7/1965  South Africa .......................... 71/92

OTHER PUBLICATIONS

Chem. Ber., 105, 2791 (1972).

Primary Examiner—Robert Gerstl

[57] ABSTRACT

Benzofuran sulfamates are useful as plant growth regulants and in particular as herbicides.

13 Claims, No Drawings

BENZOFURAN SULFAMATES

RELATED APPLICATION

This application is a continuation-in-part of my co-pending U.S. patent application Ser. No. 286,602, filed July 24, 1981 now abandoned.

BACKGROUND OF THE INVENTION

This invention relates to benzofuran sulfamates which are useful as plant growth regulators and in particular as herbicides.

Chem. Ber., 105, 2791 (1972) describes the preparation of N-butylcarbamoyl-p-toluenesulfamate, but does not claim utility as a pesticide:

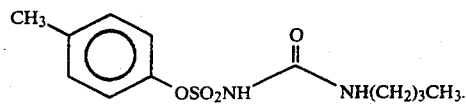

U.S. Pat. No. 4,191,553, issued on Mar. 4, 1980, to Reap discloses herbicidal compounds of the general formula:

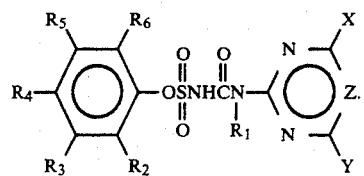

European Patent Application No. 81303180.4, published on Jan. 20, 1982, discloses herbicidal sulfamates of the general formula:

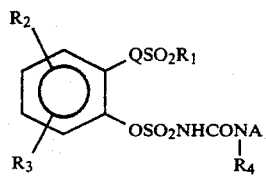

where Q is O or $NR_5$ and A can be, among others, the moiety

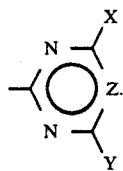

U.S. Pat. No. 4,032,649 to Singerman discloses phenolic 2,3-dihydrobenzothiophene of the formula:

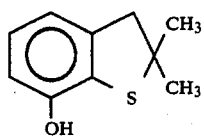

which is useful as an intermediate for the preparation of insecticidal carbamates.

South African Pat. No. 646,171 to F.M.C. Corporation discloses phenolic 2,3-dihydrobenzofurans of the general formulae:

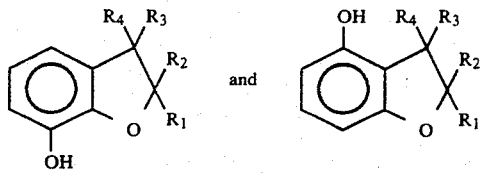

which are also useful as intermediates for the preparation of insecticidal carbamates.

Undesired vegetation can cause substantial damage to useful crops, especially agricultural products that satisfy man's basic food and fiber needs, such as cotton, rice, corn, wheat, soybean and the like.

Although a wide variety of materials are available which can be used for killing or inhibiting (controlling) the growth of undesired vegetation the need exists for still more effective herbicides that destroy or control weeds without causing significant damage to useful crops.

SUMMARY OF THE INVENTION

This invention relates to novel compounds of Formula (I) and Formula (II), suitable agricultural compositions containing them, and their method of use as general and selective pre-emergence and post-emergence herbicides, and as plant growth regulants.

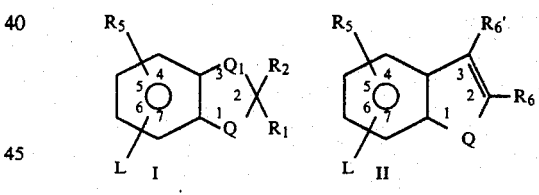

wherein
Q is O, S or $SO_2$;
$Q_1$ is $CR_3R_4$ or O;
L is $OSO_2NHCONHA$;
$R_1$ is H or $C_1$–$C_3$ alkyl;
$R_2$ is H or $CH_3$;
$R_3$ is H or $CH_3$;
$R_4$ is H or $CH_3$;
$R_5$ is H, $CH_3$, $OCH_3$, Cl, Br, $NO_2$, $CO_2R_7$, $SO_2R_8$, $OSO_2R_9$ or $SO_2NR_{10}R_{11}$;
$R_6$ is H or $C_1$–$C_3$ alkyl;
$R_6'$ is H or $CH_3$;
$R_7$ is $C_1$–$C_3$ alkyl, $CH_2CH\!\!=\!\!CH_2$, $CH_2CH_2OCH_3$ or $CH_2CH_2Cl$;
$R_8$ is $C_1$–$C_3$ alkyl;
$R_9$ is $C_1$–$C_3$ alkyl or $CF_3$;
$R_{10}$ and $R_{11}$ are independently $C_1$–$C_2$ alkyl;
A is TABLE Ia-continued

| $R_1$ | $R_2$ | $R_3$ | $R_4$ | $R_5$ | X | Y | m.p. (°C.) |
|---|---|---|---|---|---|---|---|
| CH₃ | CH₃ | H | H | CO₂CH₃ | OCH₃ | Cl | |
| CH₃ | CH₃ | H | H | CO₂CH₃ | OCH₃ | CH₂OCH₃ | |
| CH₃ | CH₃ | H | H | H | CH₃ | Cl | |
| CH₃ | CH₃ | H | H | H | CH₃ | OCH₂CH₃ | |
| CH₃ | CH₃ | H | H | H | CH₃ | CH₂OCH₃ | |
| CH₃ | H | H | H | H | CH₃ | Cl | |
| CH₃ | H | H | H | H | CH₃ | CH₂OCH₃ | |
| CH₃ | CH₃ | H | H | CH₃ | CH₃ | Cl | |
| CH₃ | CH₃ | H | H | CH₃ | CH₃ | CH₂OCH₃ | |
| CH₃ | CH₃ | H | H | Cl | CH₃ | Cl | |
| CH₃ | CH₃ | H | H | Cl | CH₃ | CH₂OCH₃ | |
| CH₂CH₃ | CH₃ | H | H | H | OCH₃ | OCH₃ | |
| CH₂CH₂CH₃ | CH₃ | H | H | H | OCH₃ | OCH₃ | |
| CH(CH₃)₂ | CH₃ | H | H | H | OCH₃ | OCH₃ | |
| CH₃ | CH₃ | H | H | H | OCH₃ | NH₂ | |
| CH₃ | CH₃ | H | H | H | OCH₃ | NHCH₃ | |
| CH₃ | CH₃ | H | H | H | OCH₃ | N(CH₃)₂ | |
| CH₃ | CH₃ | H | H | H | OCH₃ | CH(OCH₃)₂ | |
| CH₃ | CH₃ | H | H | H | OCH₃ | CH(OCH₂CH₂O) | |

TABLE Ib

| $R_1$ | $R_2$ | $R_3$ | $R_4$ | $R_5$ | X | Y | m.p. (°C.) |
|---|---|---|---|---|---|---|---|
| H | H | H | H | H | OCH₃ | OCH₃ | |
| CH₃ | CH₃ | H | H | H | OCH₃ | OCH₃ | |
| CH₃ | H | H | H | H | OCH₃ | OCH₃ | |
| H | H | CH₃ | H | H | OCH₃ | OCH₃ | |
| CH₃ | CH₃ | H | CH₃ | H | OCH₃ | OCH₃ | |
| CH₃ | CH₃ | H | H | Cl | OCH₃ | OCH₃ | |
| CH₃ | CH₃ | H | H | Br | OCH₃ | OCH₃ | |
| CH₃ | CH₃ | H | H | CH₃ | OCH₃ | OCH₃ | |
| CH₃ | CH₃ | H | H | NO₂ | OCH₃ | OCH₃ | |
| CH₃ | CH₃ | H | H | CO₂CH₃ | OCH₃ | OCH₃ | |
| CH₃ | CH₃ | H | H | SO₂N(CH₃)₂ | OCH₃ | OCH₃ | |
| CH₃ | CH₃ | H | H | OSO₂CH₃ | OCH₃ | OCH₃ | |
| CH₃ | CH₃ | H | H | OCH₃ | OCH₃ | OCH₃ | |
| H | H | H | H | H | CH₃ | OCH₃ | |
| CH₃ | CH₃ | H | H | H | CH₃ | OCH₃ | |
| CH₃ | H | H | H | H | CH₃ | OCH₃ | |
| CH₃ | H | CH₃ | H | H | CH₃ | OCH₃ | |
| CH₃ | CH₃ | H | H | Cl | CH₃ | OCH₃ | |
| CH₃ | CH₃ | H | H | CH₃ | CH₃ | OCH₃ | |
| CH₃ | CH₃ | H | H | CO₂CH₃ | CH₃ | OCH₃ | |
| H | H | H | H | H | CH₃ | CH₃ | |
| CH₃ | CH₃ | H | H | H | CH₃ | CH₃ | |
| CH₃ | H | H | H | H | CH₃ | CH₃ | |
| CH₃ | H | CH₃ | H | H | CH₃ | CH₃ | |
| CH₃ | CH₃ | H | H | Cl | CH₃ | CH₃ | |
| CH₃ | CH₃ | H | H | CH₃ | CH₃ | CH₃ | |
| CH₃ | CH₃ | H | H | CO₂CH₃ | CH₃ | CH₃ | | vents such as methylene chloride, tetrahydrofuran or acetonitrile at ambient pressure and temperature. The mode of addition is not critical; however, it is often convenient to add aryloxysulfonylisocyanate III or IV in solution to a stirred suspension of amine V. The reaction is generally exothermic. In some cases the desired product is insoluble in the warm reaction medium and crystallizes from it in pure form. Products soluble in the reaction medium are isolated by evaporation of the solvent, trituration of the solid residue with solvents such as 1-chlorobutane, hexane or ethyl ether, and filtration.

The intermediate aryloxysulfonyisocyanate III can be prepared by reacting chlorosulfonylisocyanate with an appropriately substituted 1,3-benzodiox-4-ole, 2,3-dihydrobenzofuranol, 2,3-dihydrobenzo[b]thiopheneol or 2,3-dihydrobenzo[b]thiopheneol-1,1-dioxide of Formula (VI) and heating to reflux in a solvent such as toluene or xylene according to the procedure of Lohaus, *Chem. Ber.*, 105, 2791 (1972), hereby incorporated by reference. Similarly, aryloxysulfonylisocyanate IV can be prepared by reacting chlorosulfonylisocyanate with a benzofuranol, benzo[b]thiopheneol or benzo[b]thiopheneol-1,1-dioxide of Formula (VII). Chlorosulfonylisocyanate is commercially available.

The starting 1,3-benzodiox-4-oles of Formula (VI) where Q and $Q_1$ are O, $R_5$ is H and $R_1$ and $R_2$ are as defined above are known. They can be prepared by several methods, as exemplified by U.S. Pat. No. 3,948,952 and P. J. Brooker et al., *Pestic Sci.*, 3, 735 (1972) and references therein.

The starting 2,3-dihydrobenzofuranol compounds of Formula (VI), where $R_5$ is H, Q is O, $Q_1$ is $CR_3R_4$ and $R_1$ to $R_4$ are as defined above, can be prepared by known methods. Several such methods are exemplified by Seetharamiah, *J. Chem. Soc.*, 894 (1948); Shamshurin, *Zhur. Obshchei Khim.*, 21, 2068 (1951); Neth. No. 6,500,340; Verhe, *Bull. Soc. Chim. Belg.*, 84, 747 (1975); Bhide, *Indian J. Chem. Sect. B*, 14B, 168 (1976); Neth. No. 6,515,557; Ger. Offen. No. 2,461,129; Royer, *Bull. Soc. Chim. Fr.*, 2607 (1965); and Neth. No. 6,507,520.

The starting 2,3-dihydrobenzo[b]thiopheneol compounds of Formula (VI), where $R_5$ is H, Q is S, $Q_1$ is $CR_3R_4$ and $R_1$ to $R_4$ are as defined above, can also be prepared by known methods. Several such methods are exemplified by Ger. Offen. No. 2,252,335; Kilsheimer, *J. Agr. Food Chem.*, 17, 91 (1969); U.S. Pat. No. 4,032,649; and Ger. Offen. No. 2,534,857.

Also, several starting 2,3-dihydrobenzo[b]thiopheneol-1,1-dioxide compounds of Formula (VI), where $R_5$ is H, Q is $SO_2$, $Q_1$ is $CR_3R_4$ and $R_1$ to $R_4$ are as defined above are known. They are 2,3-dihydro-4-hydroxybenzo[b]thiophene-1,1-dioxide according to Kilsheimer, *J. Agr. Food Chem.*, 17, 91 (1969); and 2,3-dihydro-2,2-dimethyl-7-hydroxy-benzo[b]thiophene-1,1-dioxide according to Ger. Offen. No. 2,534,857.

The starting benzofuranol compounds of Formula (VII) where $R_5$ is H and Q is O and $R_6$ and $R_6'$ are as defined above, can also be prepared by known methods. Several such methods are exemplified by Brit. No. 858,470; Belg. No. 670,764; Whalley, *J. Chem. Soc.*, 3224 (1951); Whalley, *J. Chem. Soc.*, 3229 (1951); Bisagni, *Bull. Soc. Chim. Fr.*, 925 (1962); Royer, *Bull. Soc. Chim. Fr.*, 1003 (1963); Neth. No. 6,507,520; Piozzi, *Org. Prep. Proc. Int.*, 3, 223 (1971); Neth. No. 6,500,340; Rene, *Bull. Soc. Chim. Fr.*, 2355 (1973); and Royer, *Bull. Soc. Chim. Fr.*, 2607 (1965).

The starting benzo[b]thiopheneol compounds of Formula (VII) are known, where $R_5$ is H and Q is S and $R_6$ and $R_6'$ are as defined above. They can be prepared by a variety of methods, as exemplified by U.S. Pat. No. 3,288,808; Napier, *J. Het. Chem.*, 7, 393 (1970); Fieser and Kennelly, *J. Am. Chem. Soc.*, 1611 (1935); U.S. Pat. No. 3,381,018; Chapman, *J. Chem. Soc. Perkin I*, 3011 (1972); Neidlein, *Tetrahedron*, 33, 3233 (1977); Ger. Offen., No. 2,252,335; Ger. Offen. No. 2,302,057; Brit. No. 1,339,883; Dulenko, *Khim. Geterotsikl Soedin*, 134 (1970), *Chem. Abs.*, 72: 90170U; Chapman, *J. Chem. Soc. Perkin Trans I*, 1404 (1972); Sunthanker, *Proc. Indiana Acad. Sci.* 33A, 35 (1951); and Kilsheimer, *J. Agr. Food Chem.*, 17, 91 (1969).

In addition, certain starting compounds of Formulae (VI) and (VII) where $R_5$ is other than H are known. These compounds are methyl 2,3-dihydro-4-hydroxy-2,2-dimethyl-5-benzofurancarboxylate according to Neth. No. 6,500,340; 5-bromo-4-hydroxybenzo[b]thiophene, 5-bromo-4-hydroxy-3-methylbenzo[b]thiophene, 4-hydroxy-5-nitrobenzo[b]thiophene and 4-hydroxy-3-methyl-5-nitrobenzo[b]thiophene according to Clarke, *J. Chem. Soc. Perkin I*, 1196 (1973); 6-bromo-7-hydroxy-3-methylbenzo[b]thiophene and 7-hydroxy-3-methyl-6-nitrobenzo[b]thiophene according to Chapman, *J. Chem. Soc. Perkin I*, 2593 (1972).

The other starting compounds of Formulae (VI) and (VII), which are not described above, can be prepared by the following general procedures.

The starting 2,3-dihydro-7-hydroxybenzofuran compounds of Formula (VIa) can be prepared as shown in Equation 3, where $R_1$ to $R_5$ are as originally defined except $R_5$ cannot be H.

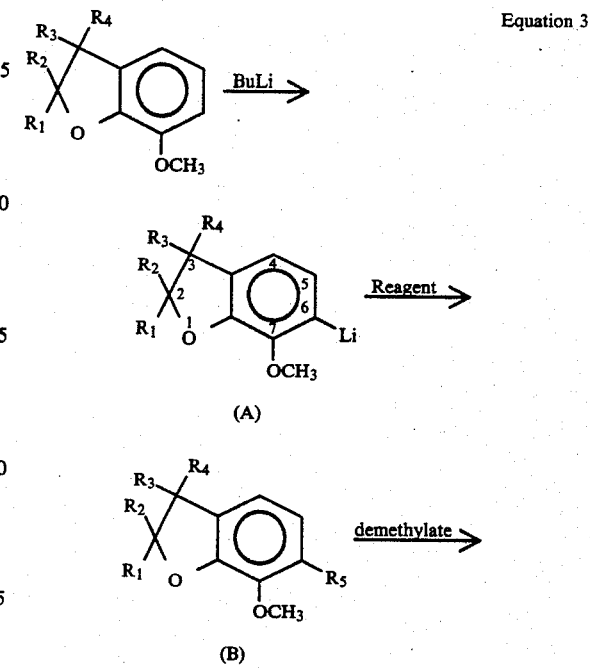

Equation 3

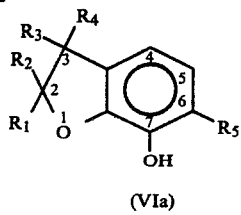

(VIa)

According to the procedure of Equation 3, a 2,3-dihydro-7-methoxybenzofuran is lithiated in the 6-position ortho to the methoxy group ("ortho" lithiation), then, after reaction with an appropriate reagent, is demethylated to provide compound (VIa). The preparation and reactions of "ortho" lithiated methoxy aryl ethers is known in the art. The subject has been reviewed by Wakefield, "The Chemistry of Organolithium Compounds," Peramon Press, New York, 1974, and by Gschwend et al., "Organic Reactions", 26, Chapter 1 (1979). Thus, the lithiation step in Equation 3 is best carried out in the usual manner, in an inert aprotic solvent such as tetrahydrofuran, ethyl ether or hexane and at a temperature in the range of $-70°$ to $50°$ C., ordinarily $-10°$ to $30°$ C. Butyllithium or other organolithium reagents can be used. The reactions are generally run from 1 to 30 hours, usually about 10 to 24 hours.

By reacting intermediate A in Equation 3 with appropriate reagents, intermediate B, where $R_5$ is $SO_2NR_{10}R_{11}$, $CO_2R_7$, $OSO_2R_9$, $SO_2R_8$, $CH_3$, $OCH_3$, Cl, Br, and $NO_2$, can be prepared. The reaction conditions for these transformations can be illustrated by the following examples:

Intermediate B where $R_5$ is $SO_2N(CH_3)_2$, for example, can be prepared by the following three step sequence: (1) a lithium sulfinate salt is formed by adding sulfur dioxide, either as a gas or in condensed form, to a suspension containing freshly prepared intermediate A, according to a procedure of Gschwend, "Organic Reactions", 26, 83 (1979) and references therein. The reaction is generally run at $-70°$ to $30°$ C., usually at about $-30°$ to $10°$ C. When the reaction is complete, usually after 0.5 to 10 hours, the solvent is evaporated to give the lithium sulfinate salt; (2) a sulfonyl chloride group is then prepared by reacting the sulfinate salt with a chlorinating agent such as N-chlorosuccinimide. The reaction is run in an inert solvent or mixtures of solvents that provide suitable solubility for both reactants. A preferred solvent is a mixture of water and an alcohol, preferably 2-propanol, in a ratio of about 2:1 water to 2-propanol. The reaction is run for 0.5 to about 2 hours and at a temperature of $0°$ to $30°$ C. Following completion of the reaction, the reaction suspension is diluted with excess water, the organic phase is extracted with methylene chloride or chloroform, and the solvent is evaporated to give B where $R_5$ is a sulfonyl chloride group; (3) the sulfonyl chloride is then reacted with excess dimethylamine in an inert solvent such as tetrahydrofuran at about $0°$ to $30°$ C. to give intermediate B where $R_5$ is $SO_2N(CH_3)_2$.

Intermediate B, where $R_5$ is $CO_2CH_3$, for example, is formed by a two step sequence: (1) a lithium carboxylate salt is formed by reacting intermediate A with carbon dioxide according to a procedure of ibid., 81 (1979) and references therein. The reaction is run by bubbling carbon dioxide gas through a suspension containing freshly prepared A at a temperature of about $-60°$ to $30°$ C., usually about $-10°$ to $10°$ C. until no further reaction occurs. The solvent is then evaporated to give the lithium carboxylate salt; (2) this salt is reacted with a methylating agent such as dimethylsulfate in water at $0°$ to $40°$ C. to give B where $R_5$ is $CO_2CH_3$. Alternatively, the $CO_2CH_3$ group can be formed by converting the lithium carboxylate salt to a carbonyl chloride group which is then reacted with methanol. The latter reactions can be run by known methods by one skilled in the art.

Intermediate B, where $R_5$ is $OSO_2CH_3$, for example, is also prepared by a two step sequence: (1) a lithium phenoxide salt is prepared by reacting intermediate A with oxygen according to a procedure of ibid., 82 (1979) and references therein. The reaction is run by bubbling oxygen through a freshly prepared suspension containing A at a temperature of $-70°$ to $30°$ C., preferably about $-10°$ to $10°$ C. until no further reaction with oxygen occurs. When the reaction is complete, usually after 1 to 24 hours, the solvent is evaporated to give the lithium phenoxide salt; (2) the salt is reacted with methanesulfonyl chloride in an inert aprotic solvent such as tetrahydrofuran at $0°$ to $40°$ C. to give B where $R_5$ is $OSO_2CH_3$.

Intermediate B, where $R_5$ is $OCH_3$ is formed also by a two step sequence: (1) a lithium phenoxide salt is prepared and isolated as previously described; and (2) the salt is reacted with an alkylating agent such as methyl iodide or dimethylsulfate to give B where $R_5$ is $OCH_3$. The reaction is generally run in an inert solvent such as tetrahydrofuran, toluene, methylene chloride or water at about $-30°$ to $60°$ C., preferably about $0°$ to $40°$ C. for 1 to about 10 hours.

Intermediate B, where $R_5$ is $SO_2CH_3$, for example, is also formed by a two step sequence: (1) a methyl mercapto group is formed by reacting freshly prepared intermediate A of Equation 3 with dimethylsulfide according to a procedure of ibid., 83 (1979) and references therein. The reaction is generally run at $-30°$ to $30°$ C., preferably about $0°$ to $25°$ C., for 0.5 to 24 hours, usually about 6 to 16 hours. Following completion of the reaction, the suspension is worked up by quenching with ice water, extracting the mixture with methylene chloride and the intermediate B is isolated where $R_5$ is $SCH_3$; (2) the $SCH_3$ group is oxidized with hydrogen peroxide, peracetic acid or meta-chloroperbenzoic acid in the usual manner to give B where $R_5$ is $SO_2CH_3$. The oxidation reaction can be run by known methods by one skilled in the art.

Intermediate B where $R_5$ is $CH_3$ is made by reacting A with dimethylsulfate according to a procedure of ibid., 81 (1979) and references therein. The reaction is generally run for 0.5 to 24 hours at $-70°$ to $30°$ C., usually at about $-30°$ to $30°$ C.

Intermediate B where $R_5$ is Cl is formed by reacting A with N-chlorosuccinimide according to a procedure of ibid, 83 (1979) and references therein. The reaction is generally run for 1 to 24 hours at $-30°$ to $30°$ C.

Intermediate B where $R_5$ is Br is formed by reacting A with a brominating agent such as bromine, 1,2-dibromoalkanes or p-toluenesulfonylbromide according to a procedure of ibid, 83 (1979) and references therein. The reactions are generally run for 1 to 24 hours at $-30°$ to $30°$ C.

Intermediate B where $R_5$ is $NO_2$ is formed by reacting A with n-propylnitrate according to a procedure of Wakefield, "The Chemistry of Organolithium Compounds," Peramon Press, New York, 1974, page 216 and references therein. The reaction is generally run for 0.5 to 10 hours at −70° to 0° C.

Demethylation of intermediate B in Equation 3 can be carried out by one of several methods known in the art. For examples, using the procedure of Royer, *Bull. Soc. Chim. Fr.*, 2607 (1965), B can be heated with excess pyridine hydrochloride at elevated temperatures for short reaction times, i.e., between 100° and 200° C. for about one-half hour, to form the demethylated product VIa; using the procedure of Neth. No. 6,500,340, B can be heated with aluminum chloride in chlorobenzene on a steam bath for short reaction times, i.e., about one-half hour, to form VIa; or using the procedure of Feutrill, *Tetrahedron Lett.*, 1327 (1970), heating B with sodium thioethoxide in dimethylformamide at about 50° to 150° C. for 0.5 to 5 hours to form VIa.

By using the reaction conditions just described, other starting compounds of Formula (VI) as well as Formula (VII) can be prepared. These reactions are shown in Equations 4–8 below.

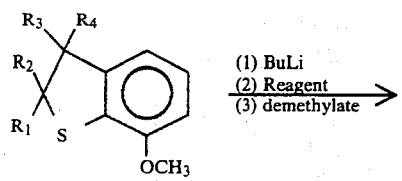

Equation 4

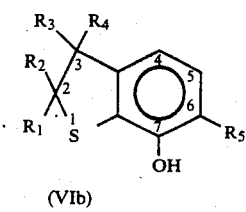

(VIb)

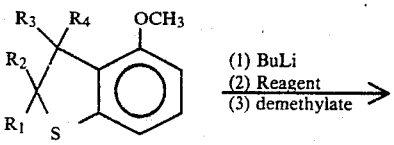

Equation 5

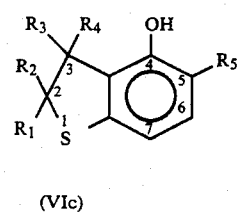

(VIc)

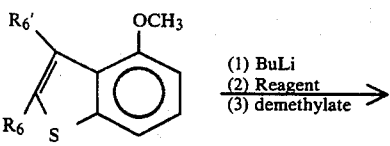

Equation 6

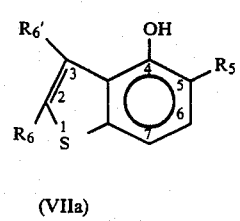

(VIIa)

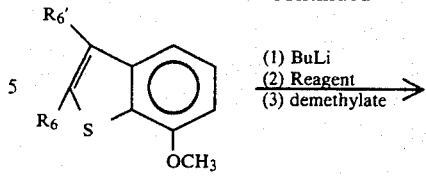

Equation 7

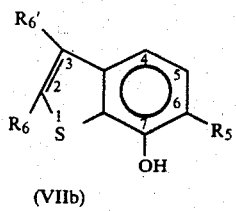

(VIIb)

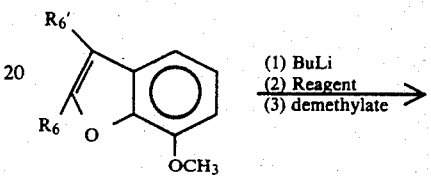

Equation 8

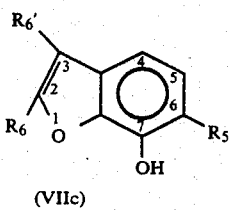

(VIIc)

The starting 2,3-dihydro-7-hydroxybenzo[b]thiophene compounds of Formula (VIb), where $R_1$ to $R_5$ are as originally defined except $R_5$ cannot be $SO_2R_8$ or H, can be prepared as shown in Equation 4. According to this equation, a 2,3-dihydro-7-methoxybenzo[b]thiophene is lithiated ortho to the methoxy group in the 6-position, then, after reaction with an appropriate reagent, is demethylated to provide compound (VIb). These reactions are run using the same reagents and conditions described in Equation 3, except that in Equation 4, the reactions are run starting with a 2,3-dihydro-7-methoxybenzo[b]thiophene.

Similarly, as shown in Equation 5, the starting 2,3-dihydro-4-hydroxybenzo[b]thiophene compounds of Formula (VIc), where $R_1$ to $R_5$ are as originally defined except $R_5$ cannot be $SO_2R_8$ or H, can be prepared. The reactions are also run using the same reagents and conditions described in Equation 3, except that in Equation 5, the reactions are run starting with a 2,3-dihydro-4-methoxybenzo[b]thiophene. In the lithiation step, although some lithiation can occur in the position ortho to the sulfur atom (7-position), lithiation occurs predominately ortho to the methoxy group in the 5-position. As reported by Gschwend, "Organic Reactions", 26, 68 (1970) and references therein, the ability of thioethers to facilitate "ortho" lithiation is less than that of ethers.

Similarly, as shown in Equation 6, the starting 4-hydroxybenzo[b]thiophene compounds of Formula (VIIa) can be prepared, where $R_6$ is $C_1$–$C_3$ alkyl and $R_6'$ is $CH_3$ and $R_5$ is as originally defined except $R_5$ cannot be H. These reactions are also run using the same reagents and conditions described in Equation 3, except that in Equation 6, the reactions are run starting with a 4-methoxybenzo[b]thiophene. In the lithiation step, some lithiation can occur in the position ortho to the sulfur atom (7-position). But, as described above in Equation 5, predominate lithiation occurs ortho to the methoxy group in the 5-position.

Similarly, as shown in Equation 7, the starting 7-hydroxybenzo[b]thiophene compounds of Formula (VIIb) can be prepared, where $R_6$ is $C_1$–$C_3$ alkyl and $R_6'$ is $CH_3$ and $R_5$ is as originally defined except $R_5$ cannot be H. These compounds are prepared using the same reagents and conditions as described in Equation 3, except in Equation 7, the reactions are run starting with a 7-methoxybenzo[b]thiophene.

Similarly, as shown in Equation 8, the starting 7-hydroxybenzofuran compounds of Formula (VIIc) can be prepared, where $R_6$ is $C_1$–$C_3$ alkyl and $R_6'$ is $CH_3$ and $R_5$ cannot be H. These compounds are also prepared using the same reagents and conditions described in Equation 3, except the reactions in Equation 8 are run starting with a 7-methoxybenzofuran.

The starting 2,3-dihydro-4-hydroxybenzofuran compounds of Formula (VI), where $Q_1$ is $CR_3R_4$ and $R_1$ to $R_5$ are as originally defined, except $R_1$ must be $C_1$–$C_3$ alkyl, can be prepared using a procedure of Neth. No. 6,500,340. The preparation involves three steps: (1) reacting at 25° to 80° C., for 1 to 8 hours, a 6-(substituted)-1,3-dihydroxybenzene with an appropriately substituted allyl chloride to form an isomeric mixture containing in part 6-(substituted)-1-hydroxy-3-allyloxybenzene; (2) separating out this compound; and (3) heating this compound at elevated temperatures 200° to 300° C. with a suitable catalyst to cause cyclization. In the first step, the reaction is run in a warm protic solvent such as ethanol in the presence of a weak base such as $K_2CO_3$. The isomers formed in the reaction can ordinarily be separated by fractional crystallization, distillation or chromatography procedures. The cyclization step is normally run neat at elevated temperatures, in the range of 100° to 300° C. A Friedel-Crafts catalyst, such as magnesium chloride, is ordinarily used to promote the cyclization reaction and increase product yields. By this method, 2,3-dihydro-4-hydroxybenzofurans of Formula (VI) can be prepared, where $R_5$ is H, $CH_3$, $OCH_3$, $SO_2NR_{10}R_{11}$, $CO_2R_7$, $OSO_2R_9$, $SO_2R_8$, Cl, Br and $NO_2$, $Q_1$ is $CR_3R_4$ and $R_1$ to $R_4$ are as defined except $R_1$ must be $C_1$–$C_3$ alkyl. Many of the starting dihydroxybenzenes are commercially available, such as 6-chloro-1,3-dihydroxybenzene. Others can be prepared from readily available materials by one skilled in the art.

Using dehydrogenation reactions, the starting 4-hydroxybenzofuran compounds of Formula (VII) can be prepared from the 2,3-dihydro-4-hydroxybenzofuran just described. The reactions can be carried out using any of several dehydrogenation procedures known in the art. Thus, using the procedure of Geisman, *J. Am. Chem. Soc.*, 72, 4326 (1950) and Hurd, *J. Am. Chem. Soc.*, 80, 4711 (1958), the compounds are dehydrogenated by the following two-step sequence: (1) the 2,3-dihydro-4-hydroxybenzofurans are heated at 60° to 80° C. for 1 to 24 hours with N-bromosuccinimide and benzoyl peroxide catalyst in an inert organic solvent such as benzene or carbon tetrachloride to cause bromination in the non-aromatic portion of the molecule, and (2) these intermediates are heated with excess N,N-dimethylaniline, either neat or in an inert aprotic solvent such as toluene for 1 to 24 hours, to cause dehydrobromination to give the benzofurans. By this method the 4-hydroxybenzofurans of Formula (VII) can be prepared, where $R_6$ is $C_1$–$C_3$ alkyl and $R_6'$ and $R_5$ are as originally defined.

The starting 2,3-dihydrobenzo[b]thiophene-1,1-dioxide compounds of Formula (VI), where Q is $SO_2$, $Q_1$ is $CR_3R_4$, $R_2$ and $R_3$ are H, $R_4$ is H or $CH_3$, $R_1$ is H or $C_1$–$C_3$ alkyl and $R_5$ is as originally defined except $R_5$ cannot be $NO_2$, can be prepared according to a 4-step procedure of Kilsheimer, *J. Agr. Food Chem.*, 17, 91 (1969). This involves (1) methylating 4- or 7-hydroxybenzo[b]thiophene of Formula (VII), where Q and $R_6$ to $R_6'$ are as defined above, with dimethylsulfate to form a methyl ester; (2) oxidizing the methyl ether to a benzo[b]thiophene-1,1-dioxide methyl ether; (3) reducing this compound to a 2,3-dihydrobenzo[b]thiophene-1,1-dioxide methyl ether; and (4) demethylating the methyl ether to form the desired phenol of Formula (VI). In the first step, the methylation is run in a warm protic solvent such as ethanol or water in the presence of a base such as $K_2CO_3$ or NaOH. The methyl ether is oxidized in the second step with 30% hydrogen peroxide in acetic acid 0° to 90° C. The resulting thiophene-1,1-dioxide is reduced by palladium on charcoal catalyst at about 25° to 50° C. at 1 to 3 atmospheres of pressure according to a procedure of Bordwell, *J. Am. Chem. Soc.*, 77, 5939 (1955). Finally, the demethylation reaction is run by heating the methyl ether with pyridine hydrochloride at elevated temperatures, at 100° to 300° C. for 0.5 to 12 hours.

The starting 2,3-dihydrobenzo[b]thiophene-1,1-dioxide compounds of Formula (VI), where Q is $SO_2$, $Q_1$ is $CR_3R_4$ and $R_1$ to $R_5$ are as originally defined, can also be prepared starting from 2,3-dihydro-4- or 7-hydroxybenzo[b]thiophene of Formula (VI), where Q is S, $Q_1$ is $CR_3R_4$ and $R_1$ to $R_5$ are as originally defined. This involves (1) methylating the compound to a methyl ether; (2) oxidizing the methyl ether to a sulfone methyl ether; and (3) demethylating the methyl ether to give the desired 2,3-dihydro-4- or 7-hydroxybenzo[b]thiophene-1,1-dioxide of Formula (VI). These reactions can be run using the same reagents and conditions described above.

By using procedures described above, the starting 4- or 7-hydroxybenzo[b]thiophene-1,1-dioxides of Formula (VII) in Equation 2 can also be prepared. Thus, by starting with an appropriately substituted 4- or 7-hydroxybenzo[b]thiophene and carrying out the methylation, oxidation and demethylation reactions described above, one skilled in the art can prepare the 4- or 7-hydroxybenzo[b]thiophene-1,1-dioxides of Formula (VII), where Q is $SO_2$ and $R_6$, $R_6'$ and $R_5$ are as defined above.

The synthesis of heterocyclic amine derivatives has been reviewed in "The Chemistry of Heterocyclic Compounds", a series published by Interscience Publ., New York and London. 2-Aminopyrimidines are described by D. J. Brown in "The Pyrimidines", Vol. XVI of the above series. 2-Amino-1,3,5-triazines are reviewed by K. R. Huffman in "The Triazines" of this same series. The synthesis of triazines are also described by F. C. Schaefer, U.S. Pat. No. 3,154,547, and by K. R. Huffman and F. C. Schaefer, *J. Org. Chem.*, 28, 1816–1821 (1963).

Also, 2-aminopyrimidines of Formula (Va) below are described by W. Braker, et al., *J. Amer. Chem. Soc.*, 69, 3072 (1947), the disclosures of which are herein incorporated by reference.

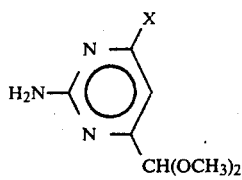

wherein X is CH₃ or OCH₃.

In addition, 2-aminotriazines of Formula (Vb) may be prepared as shown in Equation 9 below.

Equation 9

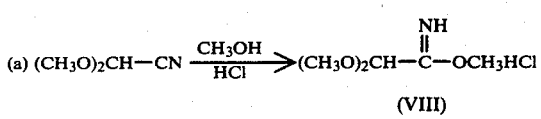

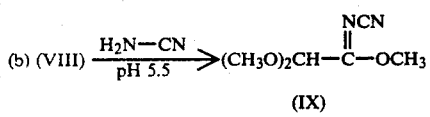

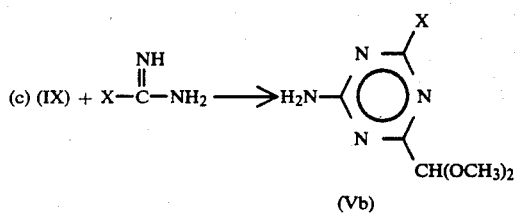

wherein X is CH₃ or OCH₃.

The reaction of Equation 9a is carried out according to the teachings of J. M. McElvain and R. L. Clarke, *J. Amer. Chem. Soc.*, 69, 2657 (1947), in which the preparation of ethyl diethoxyiminoacetate is described. The intermediate N-cyanoimidates of Formula (IX) may be prepared according to the teaching of D. Lwowski in *Synthesis*, 1971, 263, by reacting VIII with cyanamide at pH 5.5, and these may be condensed according to reaction 9c with either acetamidine or O-methyl isourea in an alcoholic solvent at 25° to 80° C. to provide the appropriate triazines.

Cyclic acetals of Formula (Vd) may be prepared from compounds of Formula (Vc) by acetal exchange as shown in Equation 10 below.

Equation 10

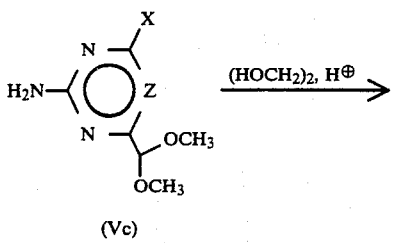

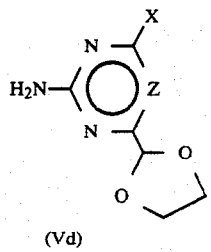

wherein
X is CH₃ or OCH₃: and
Z is CH or N.

The reaction of Equation 10 is carried out by heating the acyclic acetal in an inert solvent in the presence of one equivalent of the diol and slightly more than one equivalent of a strong acid, such as p-toluenesulfonic acid with removal of the methanol or ethanol formed in the reaction by distillation. The product is isolated by treatment with aqueous base, and extraction with an organic solvent, and purified by crystallization or column chromatography.

The compounds of this invention and their preparation are further illustrated by the following examples wherein temperatures are given in degrees centigrade and parts are by weight.

EXAMPLE 1

N,N-Dimethyl-2,3-dihydro-2,2-dimethyl-7-hydroxy-6-benzofuransulfonamide

The starting material 2,3-dihydro-2,2-dimethyl-7-benzofuranol is prepared from catechol and 3-chloro-2-methylpropene as described by Neth. No. 6,500,340. The material (16.4 g) is added to 125 ml of water and contacted with 8 ml of 50% NaOH. After stirring one-half hour, 16.4 g of dimethylsulfate is added and the resulting suspension is stirred and heated at 60° for 2 hours. The resulting mixture is extracted with methylene chloride. The organic phase is dried over sodium sulfate and the solvent is evaporated under reduced pressure. The residual oil is distilled to afford 2,3-dihydro-2,2-dimethyl-7-methoxybenzofuran.

A solution composed of 150 ml of tetrahydrofuran and 63 ml of hexane solution containing 6.4 g of n-butyl-lithium is placed in a flask and the system is purged with nitrogen. To the solution is added 17.8 g of 2,3-dihydro-2,2-dimethyl-7-methoxybenzofuran prepared above and the mixture is stirred at ambient temperature for 24 hours. The suspension, containing 2,3-dihydro-2,2-dimethyl-6-lithio-7-methoxybenzofuran, is cooled in an ice-water bath and sulfur dioxide is bubbled into the mixture while it is stirred. When absorption of sulfur dioxide ceases, the solvent is evaporated under reduced pressure. The residue is washed with ether to afford lithium 2,3-dihydro-2,2-dimethyl-7-methoxy-6-benzofuransulfinate.

To a suspension composed of 100 ml of water and 100 ml of 2-propanol and containing 24.8 g of lithium 2,3-dihydro-2,2-dimethyl-7-methoxy-6-benzofuransulfinate is added portionwise 14.7 g of N-chlorosuccinimide. The reaction temperature is maintained at 15°-20° during the addition by occasional cooling with an ice-water bath. After addition is complete, the suspension is stirred at ambient temperature for one hour and then is diluted with water. The aqueous mixture is extracted twice with methylene chloride. The combined organic extractions are dried over sodium sulfate and then the solvent is evaporated under reduced pressure to afford crude 2,3-dihydro-2,2-dimethyl-7-methoxy-6-benzofuransulfonyl chloride.

A solution of 27.6 g of crude 2,3-dihydro-2,2-dimethyl-7-methoxy-6-benzofuransulfonyl chloride dissolved in 150 ml of tetrahydrofuran is cooled in an ice-water bath and dimethylamine gas is bubbled into the suspension while stirring. When absorption of dimethylamine ceases, the suspension is stirred at ambient temperature for three hours then poured into water saturated with NaCl. The organic layer is separated and the solvent is evaporated to afford crude N,N-dimethyl-2,3-dihydro-2,2-dimethyl-7-methoxy-6-benzofuransulfonamide.

A molten suspension composed of 28.5 g of N,N-dimethyl-2,3-dihydro-2,2-dimethyl-7-methoxy-6-benzofuransulfonamide and one mole excess of pyridine hydrochloride is stirred and heated at 190° under an air condensor for 20 minutes and then is poured into ice-water. The aqueous suspension is twice extracted with methylene chloride and the combined organic extracts are dried over sodium sulfate. The solvent is removed by distillation to afford a residue containing crude N,N-dimethyl-2,3-dihydro-2,2-dimethyl-7-hydroxy-6-benzofuransulfonamide which is purified by chromatography procedures.

EXAMPLE 2

Methyl 2,3-dihydro-2,2-dimethyl-7-hydroxybenzofuran-6-carboxylate

A suspension containing 2,3-dihydro-2,2-dimethyl-6-lithio-7-methoxybenzofuran in tetrahydrofuran and hexane is prepared as described in Example 1. The suspension is cooled in an ice-water bath and carbon dioxide is bubbled into the suspension while stirring. When absorption of carbon dioxide ceases, the solvent is evaporated under reduced pressure to afford crude 2,3-dihydro-2,2-dimethyl-7-methoxy-6-benzofurancarboxylate lithium salt.

The crude compound is reacted with a 10% mole excess of dimethylsulfate in 100 ml of water at room temperature for about 3 hours to give crude methyl 2,3-dihydro-2,2-dimethyl-7-methoxybenzofuran-6-carboxylate.

This compound is reacted with one mole excess of pyridine hydrochloride, as described in Example 1, to afford crude methyl 2,3-dihydro-2,2-dimethyl-7-hydroxybenzofuran-6-carboxylate. The compound is purified by chromatography procedures.

EXAMPLE 3

6-Chloro-2,3-dihydro-2,2-dimethyl-7-benzofuranol

A suspension containing 2,3-dihydro-2,2-dimethyl-6-lithio-7-methoxybenzofuran is prepared as described in Example 1. The suspension is cooled in an ice-water bath and 13.3 g of N-chlorosuccinimide is added. The suspension is stirred at room temperature for eight hours and then acidified with cold aqueous sulfuric acid. The organic phase is separated, washed with water saturated with sodium chloride, then dried over sodium sulfate. The solvent is evaporated to give crude 6-chloro-2,3-dihydro-2,2-dimethyl-7-methoxybenzofuran.

This compound is heated with two equivalents of pyridine hydrochloride, as described in Example 1, to give crude 6-chloro-2,3-dihydro-2,2-dimethyl-7-benzofuranol. The product is purified by chromatography procedures.

EXAMPLE 4

2,3-Dihydro-2,2-dimethyl-7-benzofuranyl[(4,6-dimethoxypyrimidin-2-yl)aminocarbonyl]sulfamate To a well stirred solution of 4.9 g of 2,3-dihydro-2,2-dimethyl-7-hydroxybenzofuran in 40 ml of dry xylene at ambient temperature and pressure was added dropwise 4.2 g chlorosulfonylisocyanate over one-half hour. The resultant mixture was stirred at ambient temperature for one hour, then refluxed for one hour. The solvent was removed under reduced pressure to give a clear oil. The oil was diluted with 10 ml of tetrahydrofuran and added to a cooled (ice-water bath) suspension of 4.7 g of 2-amino-4,6-dimethoxypyrimidine in 30 ml of tetrahydrofuran. After stirring the suspension for 24 hours at ambient temperature, the solvent was removed under vacuum. The resultant solid was recrystallized from acetonitrile to give 4 g of white solid, m.p. 165°–169° C. the infrared spectrum showed characteristic absorption bands at 3150 cm$^{-1}$, 1720 cm$^{-1}$, 1625 cm$^{-1}$ and 1580 cm$^{-1}$.

By using molar equivalent amounts of an appropriate 2-aminopyrimidine and an appropriately substituted aryloxysulfonylisocyanate, the compounds of Formulae (I) and (II), set forth in Tables Ia to Im, can be prepared by the procedure of Example 4.

TABLE Ia

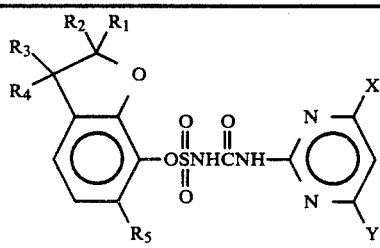

| $R_1$ | $R_2$ | $R_3$ | $R_4$ | $R_5$ | X | Y | m.p. (°C.) |
|---|---|---|---|---|---|---|---|
| H | H | H | H | H | OCH$_3$ | OCH$_3$ | |
| CH$_3$ | H | H | H | H | OCH$_3$ | OCH$_3$ | |
| H | H | CH$_3$ | H | H | OCH$_3$ | OCH$_3$ | |
| CH$_3$ | H | H | CH$_3$ | H | OCH$_3$ | OCH$_3$ | |
| H | CH$_3$ | CH$_3$ | CH$_3$ | H | OCH$_3$ | OCH$_3$ | |
| CH$_3$ | CH$_3$ | H | H | Cl | OCH$_3$ | OCH$_3$ | |
| CH$_3$ | H | H | H | Cl | OCH$_3$ | OCH$_3$ | |
| CH$_3$ | H | H | CH$_3$ | Cl | OCH$_3$ | OCH$_3$ | |
| CH$_3$ | CH$_3$ | H | H | CH$_3$ | OCH$_3$ | OCH$_3$ | |

TABLE Ia-continued

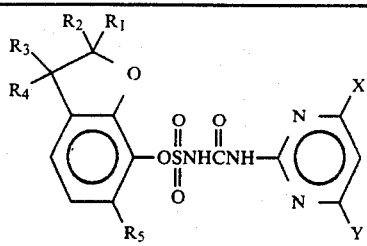

| R₁ | R₂ | R₃ | R₄ | R₅ | X | Y | m.p. (°C.) |
|---|---|---|---|---|---|---|---|
| CH₃ | H | H | H | CH₃ | OCH₃ | OCH₃ | |
| CH₃ | H | H | CH₃ | CH₃ | OCH₃ | OCH₃ | |
| CH₃ | CH₃ | H | H | NO₂ | OCH₃ | OCH₃ | |
| CH₃ | CH₃ | H | H | Br | OCH₃ | OCH₃ | |
| CH₃ | CH₃ | H | H | OCH₃ | OCH₃ | OCH₃ | |
| CH₃ | CH₃ | H | H | CO₂CH₃ | OCH₃ | OCH₃ | |
| CH₃ | CH₃ | H | H | CO₂CH₂CH₂CH₃ | OCH₃ | OCH₃ | |
| CH₃ | CH₃ | H | H | CO₂CH₂CH=CH₂ | OCH₃ | OCH₃ | |
| CH₃ | CH₃ | H | H | CO₂CH₂CH₂Cl | OCH₃ | OCH₃ | |
| CH₃ | CH₃ | H | H | SO₂CH₃ | OCH₃ | OCH₃ | |
| CH₃ | CH₃ | H | H | CO₂CH₂CH₂OCH₃ | OCH₃ | OCH₃ | |
| CH₃ | CH₃ | H | H | OSO₂CH₃ | OCH₃ | OCH₃ | |
| CH₃ | CH₃ | H | H | OSO₂CH₂CH₂CH₃ | OCH₃ | OCH₃ | |
| CH₃ | CH₃ | H | H | SO₂CH₂CH₂CH₃ | OCH₃ | OCH₃ | |
| CH₃ | CH₃ | H | H | CO₂CH₂CH₃ | OCH₃ | OCH₃ | |
| CH₃ | CH₃ | H | H | CH₂CH(CH₃)₂ | OCH₃ | OCH₃ | |
| CH₃ | CH₃ | H | H | SO₂CH₂CH₃ | OCH₃ | OCH₃ | |
| CH₃ | CH₃ | H | H | SO₂CH(CH₃)₂ | OCH₃ | OCH₃ | |
| CH₃ | CH₃ | H | H | OSO₂CH₂CH₃ | OCH₃ | OCH₃ | |
| CH₃ | CH₃ | H | H | OSO₂CH(CH₃)₂ | OCH₃ | OCH₃ | |
| CH₃ | CH₃ | H | H | OSO₂CF₃ | OCH₃ | OCH₃ | |
| CH₃ | CH₃ | H | H | SO₂N(CH₃)₂ | OCH₃ | OCH₃ | |
| CH₃ | CH₃ | H | H | SO₂N(CH₂CH₃)₂ | OCH₃ | OCH₃ | |
| CH₃ | CH₃ | H | H | SO₂N(CH₂CH₃)(CH₃) | OCH₃ | OCH₃ | |
| H | H | H | H | H | CH₃ | OCH₃ | |
| CH₃ | CH₃ | H | H | H | CH₃ | OCH₃ | 165–168° |
| CH₃ | H | H | H | H | CH₃ | OCH₃ | |
| H | H | CH₃ | H | H | CH₃ | OCH₃ | |
| CH₃ | H | H | CH₃ | H | CH₃ | OCH₃ | |
| CH₃ | CH₃ | H | H | Cl | CH₃ | OCH₃ | |
| CH₃ | H | H | H | Cl | CH₃ | OCH₃ | |
| CH₃ | H | H | CH₃ | Cl | CH₃ | OCH₃ | |
| CH₃ | CH₃ | H | H | CH₃ | CH₃ | OCH₃ | |
| CH₃ | H | H | H | CH₃ | CH₃ | OCH₃ | |
| CH₃ | H | H | CH₃ | CH₃ | CH₃ | OCH₃ | |
| CH₃ | CH₃ | H | H | NO₂ | CH₃ | OCH₃ | |
| CH₃ | CH₃ | H | H | CO₂CH₃ | CH₃ | OCH₃ | |
| CH₃ | CH₃ | H | H | SO₂CH₃ | CH₃ | OCH₃ | |
| CH₃ | CH₃ | H | H | OSO₂CH₃ | CH₃ | OCH₃ | |
| CH₃ | CH₃ | H | H | SO₂N(CH₃)₂ | CH₃ | OCH₃ | |
| CH₃ | CH₃ | H | H | OCH₃ | CH₃ | OCH₃ | |
| H | H | H | H | H | CH₃ | CH₃ | |
| CH₃ | CH₃ | H | H | H | CH₃ | CH₃ | 168–171° |
| CH₃ | H | H | H | H | CH₃ | CH₃ | |
| H | H | CH₃ | H | H | CH₃ | CH₃ | |
| CH₃ | H | H | CH₃ | H | CH₃ | CH₃ | |
| CH₃ | CH₃ | H | H | Cl | CH₃ | CH₃ | |
| CH₃ | H | H | H | Cl | CH₃ | CH₃ | |
| CH₃ | H | H | CH₃ | Cl | CH₃ | CH₃ | |
| CH₃ | CH₃ | H | H | CH₃ | CH₃ | CH₃ | |
| CH₃ | H | H | H | CH₃ | CH₃ | CH₃ | |
| CH₃ | H | H | CH₃ | CH₃ | CH₃ | CH₃ | |
| CH₃ | CH₃ | H | H | NO₂ | CH₃ | CH₃ | |
| CH₃ | CH₃ | H | H | CO₂CH₃ | CH₃ | CH₃ | |
| CH₃ | CH₃ | H | H | SO₂CH₃ | CH₃ | CH₃ | |
| CH₃ | CH₃ | H | H | OSO₂CH₃ | CH₃ | CH₃ | |
| CH₃ | CH₃ | H | H | SO₂N(CH₃)₂ | CH₃ | CH₃ | |
| CH₃ | CH₃ | H | H | OCH₃ | CH₃ | CH₃ | |
| CH₃ | CH₃ | H | H | H | OCH₃ | Cl | |
| CH₃ | CH₃ | H | H | H | OCH₃ | OCH₂CH₃ | |
| CH₃ | CH₃ | H | H | H | OCH₃ | CH₂OCH₃ | |
| CH₃ | CH₃ | H | H | Cl | OCH₃ | Cl | |
| CH₃ | CH₃ | H | H | Cl | OCH₃ | Cl | |
| CH₃ | CH₃ | H | H | CH₃ | OCH₃ | Cl | |
| CH₃ | CH₃ | H | H | CH₃ | OCH₃ | CH₂OCH₃ | |

TABLE Ia-continued

[Structure: benzofuran with R1, R2 on furan carbon adjacent to O; R3, R4 on other furan carbon; phenyl ring bearing -OSO2NHC(O)NH- linked to pyrimidine with X and Y substituents; R5 on phenyl ring]

| R₁ | R₂ | R₃ | R₄ | R₅ | X | Y | m.p. (°C.) |
|---|---|---|---|---|---|---|---|
| CH₃ | CH₃ | H | H | CO₂CH₃ | OCH₃ | Cl | |
| CH₃ | CH₃ | H | H | CO₂CH₃ | OCH₃ | CH₂OCH₃ | |
| CH₃ | CH₃ | H | H | H | CH₃ | Cl | |
| CH₃ | CH₃ | H | H | H | CH₃ | OCH₂CH₃ | |
| CH₃ | CH₃ | H | H | H | CH₃ | CH₂OCH₃ | |
| CH₃ | H | H | H | H | CH₃ | Cl | |
| CH₃ | H | H | H | H | CH₃ | CH₂OCH₃ | |
| CH₃ | CH₃ | H | H | CH₃ | CH₃ | Cl | |
| CH₃ | CH₃ | H | H | CH₃ | CH₃ | CH₂OCH₃ | |
| CH₃ | CH₃ | H | H | Cl | CH₃ | Cl | |
| CH₃ | CH₃ | H | H | Cl | CH₃ | CH₂OCH₃ | |
| CH₂CH₃ | CH₃ | H | H | H | OCH₃ | OCH₃ | |
| CH₂CH₂CH₃ | CH₃ | H | H | H | OCH₃ | OCH₃ | |
| CH(CH₃)₂ | CH₃ | H | H | H | OCH₃ | OCH₃ | |
| CH₃ | CH₃ | H | H | H | OCH₃ | NH₂ | |
| CH₃ | CH₃ | H | H | H | OCH₃ | NHCH₃ | |
| CH₃ | CH₃ | H | H | H | OCH₃ | N(CH₃)₂ | |
| CH₃ | CH₃ | H | H | H | OCH₃ | CH(OCH₃)₂ | |
| CH₃ | CH₃ | H | H | H | OCH₃ | [1,3-dioxolan-2-yl: CH bonded to two O-CH₂] | |

TABLE Ib

[Structure: isomeric benzofuran with R1, R2 on furan carbon adjacent to O; R3, R4 on other furan carbon; phenyl-OSO2NHC(O)NH-pyrimidine(X,Y); R5 on phenyl]

| R₁ | R₂ | R₃ | R₄ | R₅ | X | Y | m.p. (°C.) |
|---|---|---|---|---|---|---|---|
| H | H | H | H | H | OCH₃ | OCH₃ | |
| CH₃ | CH₃ | H | H | H | OCH₃ | OCH₃ | |
| CH₃ | H | H | H | H | OCH₃ | OCH₃ | |
| H | H | CH₃ | H | H | OCH₃ | OCH₃ | |
| CH₃ | CH₃ | H | CH₃ | H | OCH₃ | OCH₃ | |
| CH₃ | CH₃ | H | H | Cl | OCH₃ | OCH₃ | |
| CH₃ | CH₃ | H | H | Br | OCH₃ | OCH₃ | |
| CH₃ | CH₃ | H | H | CH₃ | OCH₃ | OCH₃ | |
| CH₃ | CH₃ | H | H | NO₂ | OCH₃ | OCH₃ | |
| CH₃ | CH₃ | H | H | CO₂CH₃ | OCH₃ | OCH₃ | |
| CH₃ | CH₃ | H | H | SO₂N(CH₃)₂ | OCH₃ | OCH₃ | |
| CH₃ | CH₃ | H | H | OSO₂CH₃ | OCH₃ | OCH₃ | |
| CH₃ | CH₃ | H | H | OCH₃ | OCH₃ | OCH₃ | |
| H | H | H | H | H | CH₃ | OCH₃ | |
| CH₃ | CH₃ | H | H | H | CH₃ | OCH₃ | |
| CH₃ | H | H | H | H | CH₃ | OCH₃ | |
| CH₃ | H | CH₃ | H | H | CH₃ | OCH₃ | |
| CH₃ | CH₃ | H | H | Cl | CH₃ | OCH₃ | |
| CH₃ | CH₃ | H | H | CH₃ | CH₃ | OCH₃ | |
| CH₃ | CH₃ | H | H | CO₂CH₃ | CH₃ | OCH₃ | |
| H | H | H | H | H | CH₃ | CH₃ | |
| CH₃ | CH₃ | H | H | H | CH₃ | CH₃ | |
| CH₃ | H | H | H | H | CH₃ | CH₃ | |
| CH₃ | H | CH₃ | H | H | CH₃ | CH₃ | |
| CH₃ | CH₃ | H | H | Cl | CH₃ | CH₃ | |
| CH₃ | CH₃ | H | H | CH₃ | CH₃ | CH₃ | |
| CH₃ | CH₃ | H | H | CO₂CH₃ | CH₃ | CH₃ | |

TABLE Ib-continued

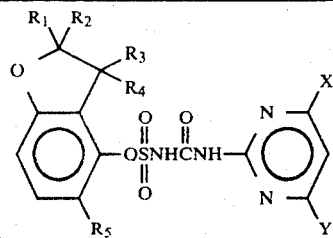

| R₁ | R₂ | R₃ | R₄ | R₅ | X | Y | m.p. (°C.) |
|----|----|----|----|----|---|---|------------|
| CH₃ | CH₃ | H | H | H | OCH₃ | Cl | |
| CH₃ | CH₃ | H | H | H | OCH₃ | OCH₂CH₃ | |
| CH₃ | CH₃ | H | H | H | OCH₃ | CH₂OCH₃ | |
| CH₃ | CH₃ | H | H | H | OCH₃ | Cl | |
| CH₃ | CH₃ | H | H | H | CH₃ | OCH₂CH₃ | |
| CH₃ | CH₃ | H | H | H | CH₃ | CH₂OCH₃ | |

TABLE Ic

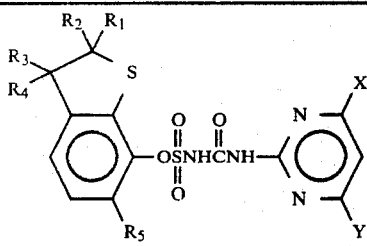

| R₁ | R₂ | R₃ | R₄ | R₅ | X | Y | m.p. (°C.) |
|----|----|----|----|----|---|---|------------|
| CH₃ | CH₃ | H | H | H | OCH₃ | OCH₃ | |
| CH₃ | H | H | H | H | OCH₃ | OCH₃ | |
| CH₃ | CH₃ | H | H | Cl | OCH₃ | OCH₃ | |
| CH₃ | H | H | H | Br | OCH₃ | OCH₃ | |
| CH₃ | CH₃ | H | H | NO₂ | OCH₃ | OCH₃ | |
| H | CH₃ | H | H | CO₂CH₃ | OCH₃ | OCH₃ | |
| CH₃ | CH₃ | H | H | SO₂N(CH₃)₂ | OCH₃ | OCH₃ | |
| CH₃ | CH₃ | H | H | OSO₂CH₃ | OCH₃ | OCH₃ | |
| CH₃ | CH₃ | H | H | CH₃ | OCH₃ | OCH₃ | |
| CH₃ | CH₃ | H | H | OCH₃ | OCH₃ | OCH₃ | |
| CH₃ | CH₃ | H | H | H | OCH₃ | CH₃ | |
| CH₃ | H | H | H | H | OCH₃ | CH₃ | |
| CH₃ | CH₃ | H | H | H | CH₃ | CH₃ | |
| CH₃ | H | H | H | H | CH₃ | CH₃ | |
| CH₃ | CH₃ | H | H | H | OCH₃ | Cl | |
| CH₃ | CH₃ | H | H | H | OCH₃ | OCH₂CH₃ | |
| CH₃ | CH₃ | H | H | H | OCH₃ | CH₂OCH₃ | |

TABLE Id

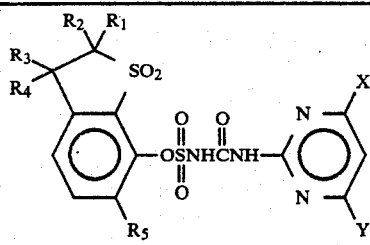

| R₁ | R₂ | R₃ | R₄ | R₅ | X | Y | m.p. (°C.) |
|----|----|----|----|----|---|---|------------|
| CH₃ | CH₃ | H | H | H | OCH₃ | OCH₃ | |
| CH₃ | H | H | H | H | OCH₃ | OCH₃ | |
| CH₃ | CH₃ | H | H | H | OCH₃ | CH₃ | |
| CH₃ | H | H | H | H | CH₃ | OCH₃ | |
| CH₃ | CH₃ | H | H | H | CH₃ | CH₃ | |
| H | CH₃ | H | H | H | CH₃ | CH₃ | |
| CH₃ | CH₃ | H | H | CO₂CH₃ | OCH₃ | OCH₃ | |
| CH₃ | CH₃ | H | H | Cl | OCH₃ | OCH₃ | |
| CH₃ | CH₃ | H | H | CH₃ | OCH₃ | OCH₃ | |

TABLE Id-continued

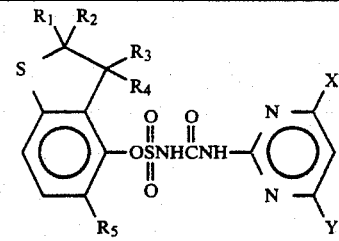

| R₁ | R₂ | R₃ | R₄ | R₅ | X | Y | m.p. (°C.) |
|----|----|----|----|----|---|---|------------|
| CH₃ | CH₃ | H | H | CH₃ | CH₃ | OCH₃ | |
| CH₃ | CH₃ | H | H | CH₃ | CH₃ | CH₃ | |

TABLE Ie

| R₁ | R₂ | R₃ | R₄ | R₅ | X | Y | m.p. (°C.) |
|----|----|----|----|----|---|---|------------|
| CH₃ | CH₃ | H | H | H | OCH₃ | OCH₃ | |
| CH₃ | CH₃ | H | H | H | CH₃ | OCH₃ | |
| CH₃ | CH₃ | H | H | H | CH₃ | CH₃ | |
| CH₃ | H | H | H | H | OCH₃ | OCH₃ | |
| CH₃ | H | H | H | H | CH₃ | OCH₃ | |
| H | CH₃ | H | H | H | CH₃ | CH₃ | |
| H | H | H | H | H | OCH₃ | OCH₃ | |
| H | H | H | H | H | CH₃ | OCH₃ | |
| H | H | H | H | H | CH₃ | CH₃ | |
| CH₃ | H | H | H | H | OCH₃ | Cl | |
| H | H | H | H | H | OCH₃ | Cl | |
| CH₃ | H | H | H | H | OCH₃ | Cl | |

TABLE If

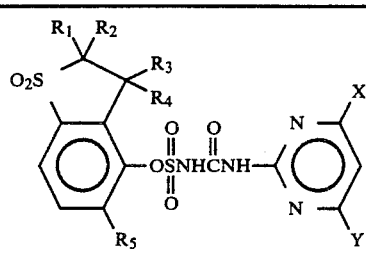

| R₁ | R₂ | R₃ | R₄ | R₅ | X | Y | m.p. (°C.) |
|---|---|---|---|---|---|---|---|
| CH₃ | CH₃ | H | H | H | OCH₃ | OCH₃ | |
| CH₃ | CH₃ | H | H | H | CH₃ | OCH₃ | |
| CH₃ | CH₃ | H | H | H | CH₃ | CH₃ | |
| CH₃ | H | H | H | H | OCH₃ | OCH₃ | |
| CH₃ | H | H | H | H | CH₃ | OCH₃ | |
| H | CH₃ | H | H | H | CH₃ | CH₃ | |
| H | H | H | H | H | OCH₃ | OCH₃ | |
| H | H | H | H | H | OCH₃ | CH₃ | |
| H | H | H | H | H | CH₃ | CH₃ | |

TABLE Ih

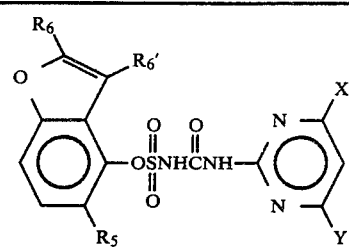

| R₅ | R₆ | R₆' | X | Y | m.p. (°C.) |
|---|---|---|---|---|---|
| H | H | H | OCH₃ | OCH₃ | |
| H | H | H | OCH₃ | CH₃ | |
| H | H | H | CH₃ | CH₃ | |
| H | CH₃ | CH₃ | OCH₃ | OCH₃ | |
| H | H | CH₃ | OCH₃ | OCH₃ | |
| H | CH₃ | H | OCH₃ | OCH₃ | |
| Cl | CH₃ | CH₃ | OCH₃ | OCH₃ | |
| CH₃ | CH₃ | CH₃ | OCH₃ | OCH₃ | |
| CO₂CH₃ | CH₃ | CH₃ | OCH₃ | OCH₃ | |

TABLE Ig

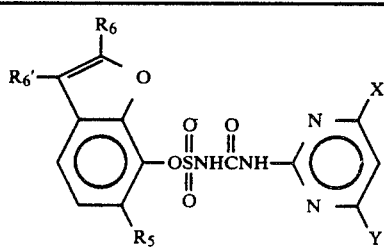

| R₅ | R₆ | R₆' | X | Y | m.p. (°C.) |
|---|---|---|---|---|---|
| H | H | H | OCH₃ | OCH₃ | |
| H | H | H | OCH₃ | CH₃ | |
| H | H | H | CH₃ | CH₃ | |
| H | CH₃ | CH₃ | OCH₃ | OCH₃ | |
| H | CH₃ | CH₃ | CH₃ | OCH₃ | |
| H | CH₃ | CH₃ | CH₃ | CH₃ | |
| H | CH₃ | H | OCH₃ | OCH₃ | |
| H | CH₃ | H | OCH₃ | CH₃ | |
| H | CH₃ | H | CH₃ | CH₃ | |
| H | H | CH₃ | OCH₃ | OCH₃ | |
| H | H | CH₃ | CH₃ | CH₃ | |
| Cl | CH₃ | CH₃ | OCH₃ | OCH₃ | |
| Br | CH₃ | CH₃ | OCH₃ | OCH₃ | |
| SO₂N(CH₃)₂ | CH₃ | CH₃ | OCH₃ | CH₃ | |
| SO₂N(CH₂CH₃)₂ | CH₃ | CH₃ | CH₃ | CH₃ | |
| SO₂CH₃ | CH₃ | CH₃ | OCH₃ | OCH₃ | |
| SO₂CH₂CH₂CH₃ | CH₃ | CH₃ | OCH₃ | OCH₃ | |
| OSO₂CH₃ | CH₃ | CH₃ | OCH₃ | OCH₃ | |
| OSO₂CH₂CH₂CH₃ | CH₃ | CH₃ | OCH₃ | OCH₃ | |
| OSO₂CF₃ | CH₃ | CH₃ | OCH₃ | OCH₃ | |
| CO₂CH₃ | CH₃ | CH₃ | OCH₃ | OCH₃ | |
| CO₂CH₂CH₂CH₃ | CH₃ | CH₃ | OCH₃ | CH₃ | |
| NO₂ | CH₃ | CH₃ | CH₃ | CH₃ | |
| OCH₃ | CH₃ | CH₃ | OCH₃ | OCH₃ | |
| CH₃ | CH₃ | CH₃ | CH₃ | CH₃ | |
| CO₂CH₂CH=CH₂ | CH₃ | CH₃ | CH₃ | CH₃ | |
| CO₂CH₂CH₂Cl | CH₃ | CH₃ | CH₃ | OCH₃ | |
| CO₂CH₂CH₂OCH₃ | CH₃ | CH₃ | CH₃ | CH₃ | |
| H | CH₂CH₃ | H | OCH₃ | OCH₃ | |
| H | CH₂CH₂CH₃ | H | OCH₃ | OCH₃ | |

TABLE Ii

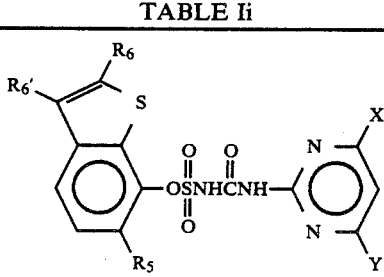

| R₅ | R₆ | R₆' | X | Y | m.p. (°C.) |
|---|---|---|---|---|---|
| H | H | H | OCH₃ | OCH₃ | |
| H | H | H | CH₃ | OCH₃ | |
| H | H | H | CH₃ | CH₃ | |
| H | CH₃ | H | OCH₃ | OCH₃ | |
| H | CH₃ | H | CH₃ | OCH₃ | |
| H | CH₃ | H | CH₃ | CH₃ | |
| H | CH₃ | CH₃ | OCH₃ | OCH₃ | |
| H | H | CH₃ | OCH₃ | OCH₃ | |
| Cl | CH₃ | CH₃ | OCH₃ | OCH₃ | |
| Br | CH₃ | CH₃ | OCH₃ | OCH₃ | |
| NO₂ | CH₃ | CH₃ | OCH₃ | OCH₃ | |
| OCH₃ | CH₃ | CH₃ | OCH₃ | OCH₃ | |
| CO₂CH₃ | CH₃ | CH₃ | OCH₃ | OCH₃ | |
| CO₂CH₂CH₂CH₃ | CH₃ | CH₃ | OCH₃ | OCH₃ | |
| CO₂CH₂CH=CH₂ | CH₃ | CH₃ | OCH₃ | OCH₃ | |
| CO₂CH₂CH₂OCH₃ | CH₃ | CH₃ | OCH₃ | OCH₃ | |
| CO₂CH₂CH₂Cl | CH₃ | CH₃ | OCH₃ | OCH₃ | |
| SO₂CH₃ | CH₃ | CH₃ | OCH₃ | OCH₃ | |
| SO₂CH₂CH₂CH₃ | CH₃ | CH₃ | OCH₃ | OCH₃ | |
| SO₂N(CH₃)₂ | CH₃ | CH₃ | OCH₃ | OCH₃ | |
| SO₂N(CH₂CH₃)₂ | CH₃ | CH₃ | OCH₃ | OCH₃ | |
| OSO₂CH₃ | CH₃ | CH₃ | OCH₃ | OCH₃ | |
| OSO₂CH₂CH₂CH₃ | CH₃ | CH₃ | OCH₃ | OCH₃ | |
| OSO₂CF₃ | CH₃ | CH₃ | OCH₃ | OCH₃ | |
| CH₃ | CH₃ | CH₃ | OCH₃ | OCH₃ | |
| H | H | H | CH₃ | Cl | |
| H | H | H | CH₃ | CH₂OCH₃ | |
| H | H | H | CH₃ | OCH₂CH₃ | |
| H | H | H | OCH₃ | CH₂OCH₃ | |

TABLE Ij

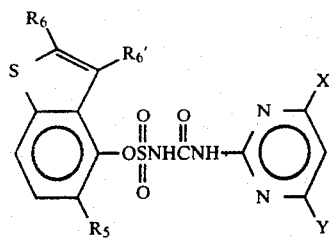

| R5 | R6 | R6' | X | Y | m.p. (°C.) |
|---|---|---|---|---|---|
| H | H | H | OCH3 | OCH3 | |
| H | H | H | OCH3 | CH3 | |
| H | H | H | CH3 | CH3 | |
| H | CH3 | H | OCH3 | OCH3 | |
| H | CH3 | H | OCH3 | CH3 | |
| H | CH3 | H | CH3 | CH3 | |
| H | CH3 | CH3 | OCH3 | OCH3 | |
| H | H | CH3 | OCH3 | OCH3 | |
| Cl | CH3 | CH3 | OCH3 | OCH3 | |
| NO2 | CH3 | CH3 | OCH3 | OCH3 | |
| CH3 | CH3 | CH3 | OCH3 | OCH3 | |
| CO2CH3 | CH3 | CH3 | OCH3 | OCH3 | |

TABLE Ik

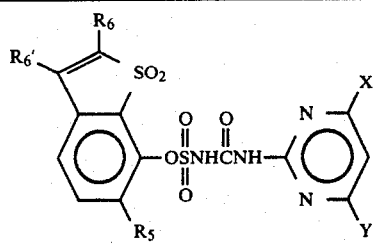

| R5 | R6 | R6' | X | Y | m.p. (°C.) |
|---|---|---|---|---|---|
| H | H | H | OCH3 | OCH3 | |
| H | H | H | OCH3 | CH3 | |
| H | H | H | CH3 | CH3 | |
| H | CH3 | H | OCH3 | OCH3 | |
| H | CH3 | H | OCH3 | CH3 | |
| H | CH3 | H | CH3 | CH3 | |
| H | CH3 | CH3 | OCH3 | OCH3 | |
| H | CH3 | CH3 | CH3 | OCH3 | |
| H | H | CH3 | OCH3 | OCH3 | |
| H | H | CH3 | CH3 | OCH3 | |
| H | H | H | OCH3 | Cl | |
| H | CH3 | H | OCH3 | Cl | |
| H | H | H | OCH3 | OC2H5 | |
| H | H | H | OCH3 | CH2OCH3 | |
| H | H | H | OCH3 | NH2 | |
| H | H | H | OCH3 | NHCH3 | |
| H | H | H | OCH3 | N(CH3)2 | |
| H | H | H | OCH3 | CH(OCH3)2 | |
| H | H | H | OCH3 |  | |
| Cl | H | H | OCH3 | OCH3 | |
| CH3 | H | H | OCH3 | OCH3 | |
| CO2CH3 | H | H | OCH3 | OCH3 | |
| H | CH2CH3 | H | OCH3 | CH3 | |
| H | CH2CH2CH3 | H | OCH3 | CH3 | |

TABLE Il

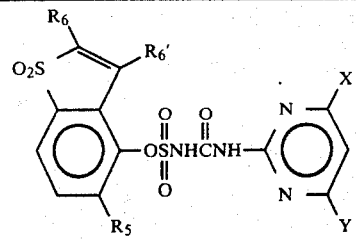

| R5 | R6 | R6' | X | Y | m.p. (°C.) |
|---|---|---|---|---|---|
| H | H | H | OCH3 | OCH3 | |
| H | H | H | CH3 | OCH3 | |
| H | H | CH3 | OCH3 | OCH3 | |
| H | CH3 | CH3 | OCH3 | OCH3 | |

TABLE Im

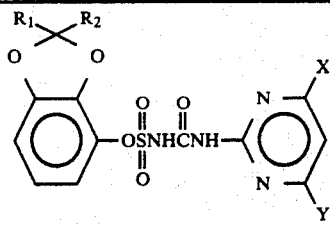

| R1 | R2 | X | Y | m.p.(°C.) |
|---|---|---|---|---|
| H | H | CH3 | CH3 | |
| H | H | OCH3 | CH3 | |
| H | H | OCH3 | OCH3 | |
| CH3 | CH3 | CH3 | CH3 | |
| CH3 | CH3 | OCH3 | CH3 | |
| CH3 | CH3 | OCH3 | OCH3 | |
| CH2CH3 | CH3 | CH3 | CH3 | |
| CH2CH3 | CH3 | OCH3 | CH3 | |
| CH2CH3 | CH3 | OCH3 | OCH3 | |
| CH2CH2CH3 | CH3 | CH3 | CH3 | |
| CH2CH2CH3 | CH3 | OCH3 | CH3 | |
| CH2CH2CH3 | CH3 | OCH3 | OCH3 | |
| CH(CH3)2 | CH3 | OCH3 | OCH3 | |
| CH(CH3)2 | CH3 | OCH3 | CH3 | |
| H | CH3 | OCH3 | OCH3 | |
| CH3 | H | OCH3 | CH3 | |
| CH3 | H | CH3 | CH3 | |
| CH2CH3 | H | OCH3 | OCH3 | |
| CH2CH3 | H | CH3 | OCH3 | |
| CH3 | CH3 | OCH3 | Cl | |
| H | H | OCH3 | Cl | |
| H | H | OCH3 | OC2H5 | |
| CH3 | CH3 | OCH3 | OC2H5 | |
| H | H | OCH3 | CH2OCH3 | |
| CH3 | CH3 | OCH3 | CH2OCH3 | |
| H | H | OCH3 | NH2 | |
| CH3 | CH3 | OCH3 | NH2 | |
| H | H | OCH3 | NHCH3 | |
| CH3 | CH3 | OCH3 | NHCH3 | |
| H | H | OCH3 | N(CH3)2 | |
| CH3 | CH3 | OCH3 | N(CH3)2 | |
| H | H | OCH3 | CH(OCH3)2 | |
| CH3 | CH3 | OCH3 | CH(OCH3)2 | |
| H | H | OCH3 |  | |
| CH3 | CH3 | OCH3 |  | |

EXAMPLE 5

2,3-Dihydro-2,2-dimethyl-7-benzofuranyl[(4,6-dimethoxy-1,3,5-triazin-2-yl)aminocarbonyl]sulfamate To a well stirred solution of 4.3 g of 2,3-dihydro-2,2-dimethyl-7-hydroxybenzofuran in 40 ml of dry xylene at ambient temperature and pressure was added dropwise 3.6 g chlorosulfonylisocyanate over one-half hour. The resultant mixture was stirred at ambient temperature for one hour and then refluxed for one hour. The solvent was removed under reduced pressure to give a clear oil. The oil was diluted with 10 ml of tetrahydrofuran and added to a cooled (ice-water bath) suspension of 3.9 g of 2-amino-4,6-dimethoxytriazine in 50 ml of tetrahydrofuran. The mixture was stirred at room temperature for 16 hours, then refluxed for 3 hours. The solvent was removed under reduced pressure to give a viscous oil. The oil was diluted with 25 ml of 1-chlorobutane and cooled to give a precipitate. The mixture was then filtered and the solid was recrystallized from the ethyl acetate to yield 2.4 g of white solid, m.p. 164°–167°. The infrared spectrum showed characteristic absorption bands at 3150 cm$^{-1}$, 1700 cm$^{-1}$, 1610 cm$^{-1}$ and 1575 cm$^{-1}$.

By using molar equivalent amounts of an appropriate 2-aminotriazine and an appropriately substituted aryloxysulfonylisocyanate, the compounds of Formulae (I) and (II) set forth in Tables IIa to IIm can be prepared by the procedure of Example 5.

TABLE IIa

| $R_1$ | $R_2$ | $R_3$ | $R_4$ | $R_5$ | X | Y | m.p.(°C.) |
|---|---|---|---|---|---|---|---|
| H | H | H | H | H | OCH$_3$ | OCH$_3$ | |
| CH$_3$ | H | H | H | H | OCH$_3$ | OCH$_3$ | |
| CH$_3$ | CH$_3$ | H | H | Cl | OCH$_3$ | OCH$_3$ | |
| CH$_3$ | CH$_3$ | H | H | CH$_3$ | OCH$_3$ | OCH$_3$ | |
| CH$_3$ | CH$_3$ | H | H | CO$_2$CH$_3$ | OCH$_3$ | OCH$_3$ | |
| H | H | H | H | H | CH$_3$ | OCH$_3$ | |
| CH$_3$ | CH$_3$ | H | H | H | CH$_3$ | OCH$_3$ | 140–143° |
| H | CH$_3$ | H | H | H | CH$_3$ | OCH$_3$ | |
| CH$_3$ | H | CH$_3$ | H | H | CH$_3$ | OCH$_3$ | |
| CH$_3$ | CH$_3$ | H | CH$_3$ | H | CH$_3$ | OCH$_3$ | |
| H | H | H | H | H | CH$_3$ | CH$_3$ | |
| CH$_3$ | CH$_3$ | H | H | H | CH$_3$ | CH$_3$ | 143–146° |
| CH$_3$ | H | H | H | H | CH$_3$ | CH$_3$ | |
| CH$_3$ | CH$_3$ | H | H | Br | OCH$_3$ | OCH$_3$ | |
| CH$_3$ | CH$_3$ | H | H | OCH$_3$ | OCH$_3$ | OCH$_3$ | |
| CH$_3$ | CH$_3$ | H | H | CO$_2$CH$_2$CH$_2$CH$_3$ | OCH$_3$ | OCH$_3$ | |
| CH$_3$ | CH$_3$ | H | H | CO$_2$CH$_2$CH=CH$_2$ | OCH$_3$ | OCH$_3$ | |
| CH$_3$ | CH$_3$ | H | H | CO$_2$CH$_2$CH$_2$Cl | OCH$_3$ | OCH$_3$ | |
| CH$_3$ | CH$_3$ | H | H | SO$_2$CH$_3$ | OCH$_3$ | OCH$_3$ | |
| CH$_3$ | CH$_3$ | H | H | SO$_2$CH$_2$CH$_2$CH$_3$ | OCH$_3$ | OCH$_3$ | |
| CH$_3$ | CH$_3$ | H | H | OSO$_2$CH$_3$ | OCH$_3$ | OCH$_3$ | |
| CH$_3$ | CH$_3$ | H | H | OSO$_2$CH$_2$CH$_2$CH$_3$ | OCH$_3$ | OCH$_3$ | |
| CH$_3$ | CH$_3$ | H | H | OSO$_2$CF$_3$ | OCH$_3$ | OCH$_3$ | |
| CH$_3$ | CH$_3$ | H | H | SO$_2$N(CH$_3$)$_2$ | OCH$_3$ | OCH$_3$ | |
| CH$_3$ | CH$_3$ | H | H | SO$_2$N(CH$_2$CH$_3$)$_2$ | OCH$_3$ | OCH$_3$ | |
| CH$_3$ | CH$_3$ | H | H | CO$_2$CH$_2$CH$_2$OCH$_3$ | OCH$_3$ | OCH$_3$ | |
| CH$_3$ | CH$_3$ | H | H | NO$_2$ | OCH$_3$ | OCH$_3$ | |
| CH$_3$ | CH$_3$ | H | H | H | OCH$_3$ | CH$_2$OCH$_3$ | |
| CH$_3$ | CH$_3$ | H | H | H | OCH$_3$ | OC$_2$H$_5$ | |
| CH$_3$ | CH$_3$ | H | H | H | CH$_3$ | OC$_2$H$_5$ | |
| CH$_3$ | CH$_3$ | H | H | H | OCH$_3$ | NH$_2$ | |
| CH$_3$ | CH$_3$ | H | H | H | OCH$_3$ | NHCH$_3$ | |
| CH$_3$ | CH$_3$ | H | H | H | OCH$_3$ | N(CH$_3$)$_2$ | |
| CH$_3$ | CH$_3$ | H | H | H | OCH$_3$ | Cl | |
| CH$_3$ | CH$_3$ | H | H | H | OCH$_3$ | CH(OCH$_3$)$_2$ | |
| CH$_3$ | CH$_3$ | H | H | H | OCH$_3$ | CH(-O-/-O-) | |
| CH$_2$CH$_3$ | CH$_3$ | H | H | H | OCH$_3$ | CH$_3$ | |
| CH$_2$CH$_2$CH$_3$ | CH$_3$ | H | H | H | OCH$_3$ | CH$_3$ | |
| CH(CH$_3$)$_2$ | CH$_3$ | H | H | H | OCH$_3$ | CH$_3$ | |

TABLE IIb

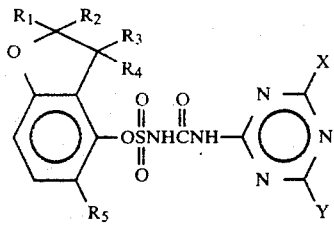

| R₁ | R₂ | R₃ | R₄ | R₅ | X | Y | m.p.(°C.) |
|---|---|---|---|---|---|---|---|
| H | H | H | H | H | OCH₃ | OCH₃ | |
| CH₃ | CH₃ | H | H | H | OCH₃ | OCH₃ | |
| CH₃ | H | H | H | H | OCH₃ | OCH₃ | |
| CH₃ | CH₃ | H | H | H | CH₃ | OCH₃ | |
| CH₃ | CH₃ | H | H | H | CH₃ | CH₃ | |
| CH₃ | CH₃ | H | H | CO₂CH₃ | CH₃ | OCH₃ | |
| CH₃ | CH₃ | H | H | Cl | CH₃ | OCH₃ | |
| CH₃ | CH₃ | H | H | CH₃ | CH₃ | OCH₃ | |

TABLE IIc

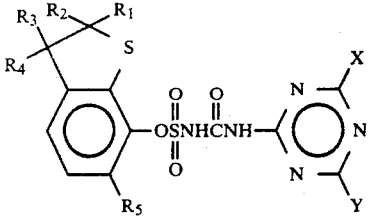

| R₁ | R₂ | R₃ | R₄ | R₅ | X | Y | m.p.(°C.) |
|---|---|---|---|---|---|---|---|
| H | H | H | H | H | OCH₃ | OCH₃ | |
| H | H | H | H | H | CH₃ | OCH₃ | |
| CH₃ | CH₃ | H | H | H | OCH₃ | OCH₃ | |
| CH₃ | CH₃ | H | H | H | CH₃ | OCH₃ | |
| CH₃ | CH₃ | H | H | H | CH₃ | CH₃ | |
| CH₃ | CH₃ | H | H | Cl | OCH₃ | OCH₃ | |
| CH₃ | CH₃ | H | H | CH₃ | CH₃ | OCH₃ | |
| CH₃ | CH₃ | H | H | CO₂CH₃ | CH₃ | OCH₃ | |

TABLE IId

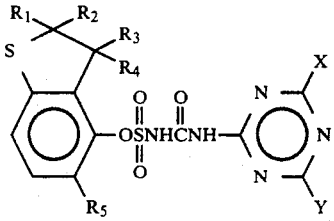

| R₁ | R₂ | R₃ | R₄ | R₅ | X | Y | m.p.(°C.) |
|---|---|---|---|---|---|---|---|
| H | H | H | H | H | OCH₃ | CH₃ | |
| CH₃ | CH₃ | H | H | H | CH₃ | OCH₃ | |
| CH₃ | CH₃ | H | H | H | OCH₃ | OCH₃ | |
| CH₃ | H | H | H | H | OCH₃ | CH₃ | |
| CH₃ | H | H | H | H | OCH₃ | OCH₃ | |
| H | H | CH₃ | H | H | CH₃ | OCH₃ | |
| H | H | H | CH₃ | H | CH₃ | CH₃ | |
| CH₃ | CH₃ | H | H | Cl | OCH₃ | OCH₃ | |
| CH₃ | CH₃ | H | H | CH₃ | OCH₃ | OCH₃ | |
| CH₃ | CH₃ | H | H | CO₂CH₃ | OCH₃ | OCH₃ | |

TABLE IIe

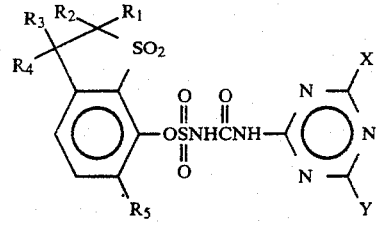

| R₁ | R₂ | R₃ | R₄ | R₅ | X | Y | m.p.(°C.) |
|---|---|---|---|---|---|---|---|
| H | H | H | H | H | OCH₃ | CH₃ |  |
| H | H | H | H | H | OCH₃ | OCH₃ | |
| CH₃ | CH₃ | H | H | H | OCH₃ | CH₃ | |
| CH₃ | H | H | H | H | CH₃ | OCH₃ | |
| H | H | CH₃ | H | H | OCH₃ | OCH₃ | |
| H | H | CH₃ | H | H | CH₃ | CH₃ | |
| CH₃ | CH₃ | H | H | Cl | OCH₃ | CH₃ | |
| CH₃ | CH₃ | H | H | CH₃ | OCH₃ | CH₃ | |
| CH₃ | CH₃ | H | H | CO₂CH₃ | OCH₃ | CH₃ | |

TABLE IIf

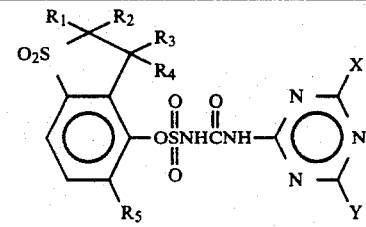

| R₁ | R₂ | R₃ | R₄ | R₅ | X | Y | m.p.(°C.) |
|---|---|---|---|---|---|---|---|
| H | H | H | H | H | OCH₃ | OCH₃ | |
| CH₃ | CH₃ | H | H | H | OCH₃ | CH₃ | |
| CH₃ | H | H | H | H | OCH₃ | OCH₃ | |
| H | H | CH₃ | H | H | CH₃ | CH₃ | |
| H | H | H | CH₃ | Cl | OCH₃ | OCH₃ | |
| CH₃ | CH₃ | H | H | CO₂CH₃ | OCH₃ | CH₃ | |
| CH₃ | CH₃ | H | H | CH₃ | OCH₃ | CH₃ | |

TABLE IIg

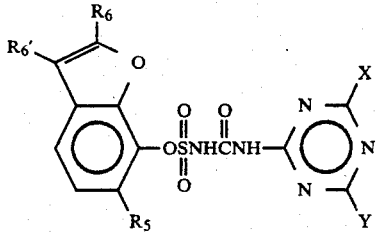

| R₅ | R₆ | R₆' | X | Y | m.p.(°C.) |
|---|---|---|---|---|---|
| H | H | H | OCH₃ | OCH₃ | |
| H | H | H | CH₃ | OCH₃ | |
| H | CH₃ | H | OCH₃ | OCH₃ | |
| H | H | CH₃ | OCH₃ | CH₃ | |
| H | CH₃ | CH₃ | OCH₃ | CH₃ | |
| Cl | CH₃ | CH₃ | OCH₃ | CH₃ | |
| CO₂CH₃ | CH₃ | CH₃ | CH₃ | OCH₃ | |
| CH₃ | CH₃ | CH₃ | OCH₃ | OCH₃ | |
| H | H | H | OCH₃ | Cl | |
| H | H | H | OCH₃ | OC₂H₅ | |
| H | H | H | OCH₃ | CH₂OCH₃ | |
| H | H | H | OCH₃ | NH₂ | |
| H | H | H | OCH₃ | NHCH₃ | |
| H | H | H | OCH₃ | N(CH₃)₂ | |
| H | H | H | OCH₃ | CH(OCH₃)₂ | |

TABLE IIg-continued

| R5 | R6 | R6' | X | Y | m.p. (°C) |
|---|---|---|---|---|---|
| H | H | H | OCH3 | $\begin{smallmatrix}O\\\ \ CH\\\ \ \ \ \ O\end{smallmatrix}$ (dioxolane) | |
| H | CH2CH3 | H | OCH3 | CH3 | |
| H | CH2CH2CH3 | H | OCH3 | CH3 | |

TABLE IIh

| R5 | R6 | R6' | X | Y | m.p. (°C) |
|---|---|---|---|---|---|
| H | H | H | OCH3 | OCH3 | |
| H | CH3 | H | CH3 | OCH3 | |
| H | H | CH3 | OCH3 | OCH3 | |
| H | CH3 | CH3 | OCH3 | CH3 | |
| Cl | CH3 | CH3 | OCH3 | CH3 | |
| CH3 | CH3 | CH3 | OCH3 | CH3 | |
| CO2CH3 | CH3 | CH3 | OCH3 | OCH3 | |

TABLE IIi

| R5 | R6 | R6' | X | Y | m.p. (°C) |
|---|---|---|---|---|---|
| H | H | H | OCH3 | OCH3 |  |
| H | CH3 | H | OCH3 | CH3 |  |
| H | H | CH3 | OCH3 | CH3 |  |
| H | CH3 | CH3 | CH3 | OCH3 |  |
| Cl | CH3 | CH3 | CH3 | OCH3 |  |
| CH3 | CH3 | CH3 | CH3 | OCH3 |  |
| CO2CH3 | CH3 | CH3 | CH3 | OCH3 |  |

TABLE IIj

| R5 | R6 | R6' | X | Y | m.p. (°C) |
|---|---|---|---|---|---|
| H | H | H | OCH3 | OCH3 | |
| H | CH3 | H | CH3 | OCH3 | |
| H | H | CH3 | CH3 | OCH3 | |
| H | CH3 | CH3 | OCH3 | CH3 | |
| CH3 | CH3 | CH3 | OCH3 | CH3 | |
| Cl | CH3 | CH3 | OCH3 | CH3 | |
| CO2CH3 | CH3 | CH3 | OCH3 | OCH3 | |

TABLE IIk

| R5 | R6 | R6' | X | Y | m.p. (°C) |
|---|---|---|---|---|---|
| H | H | H | OCH3 | OCH3 | |
| H | H | H | CH3 | OCH3 | |
| H | H | H | CH3 | CH3 | |
| H | CH3 | H | OCH3 | OCH3 | |
| H | CH3 | H | CH3 | OCH3 | |
| H | CH3 | H | CH3 | CH3 | |
| H | CH3 | CH3 | OCH3 | CH3 | |
| H | CH3 | CH3 | OCH3 | OCH3 | |
| H | H | H | OCH3 | Cl | |
| H | H | H | OCH3 | OC2H5 | |
| H | H | H | OCH3 | CH2OCH3 | |
| H | H | H | OCH3 | NH2 | |
| H | H | H | OCH3 | NHCH3 | |
| H | H | H | OCH3 | N(CH3)2 | |
| H | H | H | OCH3 | CH(OCH3)2 | |
| H | H | H | OCH3 | $\begin{smallmatrix}O\\\ \ CH\\\ \ \ \ \ O\end{smallmatrix}$ (dioxolane) | |
| H | CH2CH3 | H | OCH3 | CH3 | |
| H | CH2CH2CH3 | H | OCH3 | CH3 | |

TABLE III

| R5 | R6 | R6' | X | Y | m.p. (°C) |
|---|---|---|---|---|---|
| H | H | H | OCH3 | OCH3 | |
| H | H | H | CH3 | OCH3 | |

TABLE III-continued

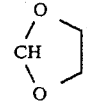

| $R_5$ | $R_6$ | $R_6'$ | X | Y | m.p. (°C.) |
|---|---|---|---|---|---|
| H | H | $CH_3$ | $OCH_3$ | $OCH_3$ | |
| H | $CH_3$ | $CH_3$ | $OCH_3$ | $OCH_3$ | |

TABLE IIm

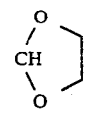

| $R_1$ | $R_2$ | X | Y | m.p. (°C.) |
|---|---|---|---|---|
| H | H | $OCH_3$ | $OCH_3$ | |
| H | H | $OCH_3$ | $CH_3$ | |
| H | H | $CH_3$ | $CH_3$ | |
| $CH_3$ | $CH_3$ | $OCH_3$ | $OCH_3$ | |
| $CH_3$ | $CH_3$ | $OCH_3$ | $CH_3$ | |
| $CH_3$ | $CH_3$ | $CH_3$ | $CH_3$ | |
| $CH_2CH_3$ | $CH_3$ | $OCH_3$ | $OCH_3$ | |
| $CH_2CH_3$ | $CH_3$ | $OCH_3$ | $CH_3$ | |
| $CH_2CH_2CH_3$ | $CH_3$ | $OCH_3$ | $OCH_3$ | |
| $CH_2CH_2CH_3$ | $CH_3$ | $CH_3$ | $OCH_3$ | |
| $CH(CH_3)_2$ | $CH_3$ | $OCH_3$ | $OCH_3$ | |
| $CH(CH_3)_2$ | $CH_3$ | $CH_3$ | $OCH_3$ | |
| H | $CH_3$ | $OCH_3$ | $OCH_3$ | |
| H | $CH_3$ | $OCH_3$ | $CH_3$ | |
| $CH_2CH_3$ | H | $OCH_3$ | $OCH_3$ | |
| $CH_2CH_3$ | H | $OCH_3$ | $CH_3$ | |
| $CH_3$ | $CH_3$ | $OCH_3$ | $CH_2OCH_3$ | |
| H | H | $OCH_3$ | $CH_2OCH_3$ | |
| H | H | $OCH_3$ | $OC_2H_5$ | |
| $CH_3$ | $CH_3$ | $OCH_3$ | $OC_2H_5$ | |
| H | H | $CH_3$ | $OC_2H_5$ | |
| $CH_3$ | $CH_3$ | $CH_3$ | $OC_2H_5$ | |
| H | H | $OCH_3$ | $NH_2$ | |
| $CH_3$ | $CH_3$ | $OCH_3$ | $NH_2$ | |
| H | H | $OCH_3$ | $NHCH_3$ | |
| $CH_3$ | $CH_3$ | $OCH_3$ | $NHCH_3$ | |
| H | H | $OCH_3$ | $N(CH_3)_2$ | |
| $CH_3$ | $CH_3$ | $OCH_3$ | $N(CH_3)_2$ | |
| H | H | $OCH_3$ | Cl | |
| $CH_3$ | $CH_3$ | $OCH_3$ | Cl | |
| H | H | $OCH_3$ | $CH(OCH_3)_2$ | |
| $CH_3$ | $CH_3$ | $OCH_3$ | $CH(OCH_3)_2$ | |
| H | H | $OCH_3$ | dioxolane | |
| $CH_3$ | $CH_3$ | $OCH_3$ | dioxolane | |

Formulations

Useful formulations of the compounds of Formulae (I) and (II) can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE III

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 6

Wettable Powder

N-[(4,6-dimethoxypyrimidin-2-yl)aminocarbonyl]sulfamic acid, 2,3-dihydro-2,2-dimethylbenzofuran-7-yl ester: 80%
sodium alkylnaphthalenesulfonate: 2%
sodium ligninsulfonate: 2%
synthetic amorphous silica: 3%
kaolinite: 13%

The ingredients are blended, hammer-milled until all the solids are essentially under 50 microns, reblended, and packaged.

EXAMPLE 7

Wettable Powder

N-[(4,6-dimethoxy-1,3,5-triazin-2-yl))aminocarbonyl]sulfamic acid, 2,3-dihydro-2,2-dimethylbenzofuran-7-yl ester: 50%
sodium alkylnaphthalenesulfonate: 2%
low viscosity methyl cellulose: 2%
diatomaceous earth: 46%

The ingredients are blended, coarsely hammer-milled and then air-milled to produce particles essentially all below 10 microns in diameter. The product is reblended before packaging.

EXAMPLE 8

Granule

Wettable Powder of Example 7: 5%
attapulgite granules (U.S.S. 20–40 mesh; 0.84–0.42 mm): 95%

A slurry of wettable powder containing ≈25% solids is sprayed on the surface of attapulgite granules in a double-cone blender. The granules are dried and packaged.

EXAMPLE 9

Extruded Pellet

N-[(4,6-dimethyl-1,3,5-triazin-2-yl)aminocarbonyl]sulfamic acid, 2,3-dihydro-2,2-dimethylbenzofuran-7-yl ester: 25%
anhydrous sodium sulfate: 10%
crude calcium ligninsulfonate: 5%
sodium alkylnaphthalenesulfonate: 1%
calcium/magnesium bentonite: 59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 10

Oil Suspension

N-[(4-methyl-6-methoxy-1,3,5-triazin-2-yl)aminocarbonyl]sulfamic acid, 2,3-dihydro-2,2-dimethylbenzofuran-7-yl ester: 25%
polyoxyethylene sorbitol hexaoleate: 5%
highly aliphatic hydrocarbon oil: 70%

The ingredients are ground together in a sand mill until the solid particles have been reduced to under about 5 microns. The resulting thick suspension may be applied directly, but preferably after being extended with oils or emulsified in water.

EXAMPLE 11

Wettable Powder

N-[(4,6-dimethyl-1,3,5-triazin-2-yl)aminocarbonyl]sulfamic acid, 2,3-dihydro-2,2-dimethylbenzofuran-7-yl ester: 20%
sodium alkylnaphthalenesulfonate: 4%
sodium ligninsulfonate: 4%
low viscosity methyl cellulose: 3%
attapulgite: 69%

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 12

Low Strength Granule

N-[(4,6-dimethoxypyrimidin-2-yl)aminocarbonyl]sulfamic acid, 2,3-dihydro-2,2-dimethylbenzofuran-7-yl ester: 1%
N,N-dimethylformamide: 9%
attapulgite granules (U.S.S. 20–40 sieve): 90%

The active ingredient is dissolved in the solvent and the solution is sprayed upon dedusted granules in a double cone blender. After spraying of the solution has been completed, the blender is allowed to run for a short period and then the granules are packaged.

EXAMPLE 13

Aqueous Suspension

N-[(4,6-dimethylpyrimidin-2-yl)aminocarbonyl]sulfamic acid, 2,3-dihydro-2,2-dimethylbenzofuran-7-yl ester: 40%
polyacrylic acid thickener: 0.3%
dodecylphenol polyethylene glycol ether: 0.5%
disodium phosphate: 1%
monosodium phosphate: 0.5%
polyvinyl alcohol: 1.0%
water: 56.7%

The ingredients are blended and ground together in a sand mill to produce particles essentially all under 5 microns in size.

EXAMPLE 14

Solution

N-[(4-methyl-6-methoxypyrimidin-2-yl)aminocarbonyl]sulfamic acid, 2,3-dihydro-2,2-dimethylbenzofuran-7-yl ester, sodium salt: 5%
water: 95%

The salt is added directly to the water with stirring to produce the solution, which may then be packaged for use.

EXAMPLE 15

Low Strength Granule

N-[(4-methyl-6-methoxy-1,3,5-triazin-2-yl)aminocarbonyl]sulfamic acid, 2,3-dihydro-2,2-dimethylbenzofuran-7-yl ester: 0.1%
attapulgite granules (U.S.S. 20-40 mesh): 99.9%

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 16

Granule

N-[(4,6-dimethoxy-1,3,5-triazin-2-yl)aminocarbonyl]sulfamic acid, 2,3-dihydro-2,2-dimethylbenzofuran-7-yl ester: 80%
wetting agent: 1%
crude ligninsulfonate salt (containing 5–20% of the natural sugars): 10%
attapulgite clay: 9%

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410-149 microns), and packaged for use.

EXAMPLE 17

High Strength Concentrate

N-[(4,6-dimethylpyrimidin-2-yl)aminocarbonyl]sulfamic acid, 2,3-dihydro-2,2-dimethylbenzofuran-7-yl ester: 99%
silica aerogel: 0.5%
synthetic amorphous silica: 0.5%

The ingredients are blended and ground in a hammer-mill to produce a material essentially all passing a U.S.S. No. 50 screen (0.3 mm opening). The concentrate may be formulated further if necessary.

EXAMPLE 18

Wettable Powder

N-[(4-methyl-6-methoxypyrimidin-2-yl)aminocarbonyl]sulfamic acid, 2,3-dihydro-2,2-dimethylbenzofuran-7-yl ester: 90%
dioctyl sodium sulfosuccinate: 0.1%
synthetic fine silica: 9.9%

The ingredients are blended and ground in a hammermill to produce particles essentially all below 100 microns. The material is sifted through a U.S.S. No. 50 screen and then packaged.

Utility

The compounds of the present invention have herbicidal properties. Some of the compounds have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, some of the subject compounds are useful for selective weed control in crops such as wheat.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.05 to 10 kg/ha, the lower rates being suggested for use on lighter soils and/or those having a low organic matter content, for selective weed control or for situations where only short-term persistence is required.

The compounds of the invention may be used in combination with any other commercial herbicide, examples of which are those of the triazine, triazole, uracil, urea, amide, diphenylether, carbamate and bipyridylium types.

The herbicidal properties of the subject compounds were discovered in a number of greenhouse tests. The test procedures and results follow.

Test A

Seeds of crabgrass (Digitaria spp.), barnyardgrass (Echinochloa crusgalli), wild oats (Avena fatua), cassia (Cassia tora), morningglory (Ipomoea sp.), cocklebur (Xanthium sp.), sorghum, corn, soybean, rice, wheat and nutsedge tubers (Cyperus rotundus) were planted in a growth medium and treated pre-emergence with the chemicals dissolved in a non-phytotoxic solvent. At the same time, cotton having fine leaves (including cotyledonary ones), bush beans with the third trifoliolate leaf expanding, crabgrass, barnyardgrass and wild oats with two leaves, cassia with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three to five leaves were sprayed. Treated plants and controls were maintained in a greenhouse for sixteen days, whereupon all species were compared to controls and visually rated for response to treatment.

The ratings are based on a numerical scale extending from 0=no injury, to 10=complete kill. The accompanying descriptive symbols have the following meanings:
C=chlorosis or necrosis;
E=emergence inhibition;
G=growth retardation;
H=formative effects; and
6Y=abscised buds or flowers.

The ratings for the compound tested by this procedure are presented in Table A. It will be seen that the compound has utility for selective weed control in wheat.

TABLE A

POST-EMERGENCE

| | Rate kg/ha | Bush bean | Cotton | Morning-glory | Cockle-bur | Cassia | Nut-sedge | Crab-grass | Barn-yard-grass | Wild Oats | Wheat | Corn | Soy-bean | Rice | Sor-ghum |
|---|---|---|---|---|---|---|---|---|---|---|---|---|---|---|---|
| Compound 1 | 0.4 | 5C, 5G, 6Y | 3C, 2H, 5G | 4C,8G | 9C | 3C | 2C,8G | 2G | 2C,8H | 0 | 0 | 2C,6H | 6C,9G | 1C,4G | 2C,9H |
| Compound 2 | 0.4 | 2C, 4H | 3C, 5G | 2C,9G | 2C,9G | 2C,5G | 0 | 2G | 1H | 0 | 0 | 2H | 3C,9G | 0 | 1C,4G |
| Compound 3 | 0.4 | 2C | 0 | 6G | 0 | 0 | 0 | 0 | 0 | 0 | 0 | 0 | 2G | 0 | 4G |
| Compound 4 | 0.4 | 1C, 5H | 1C | 5C,9G | 5C,9G | 1C,3G | 0 | 0 | 1H | 0 | 0 | 3G | 2C,9G | 2G | 2C,7H |

Compound 1: 4,6-dimethoxypyrimidin-2-yl urea sulfonamide with 2,2-dimethyl-2,3-dihydrobenzofuran Compound 2: 4-methyl-6-methoxypyrimidin-2-yl urea sulfonamide with 2,2-dimethyl-2,3-dihydrobenzofuran Compound 3: 4,6-dimethylpyrimidin-2-yl urea sulfonamide with 2,2-dimethyl-2,3-dihydrobenzofuran Compound 4: 4,6-dimethoxy-1,3,5-triazin-2-yl urea sulfonamide with 2,2-dimethyl-2,3-dihydrobenzofuran

TABLE A-continued

| Compound | Rate kg/ha | Morning-glory | Cocklebur | Cassia | Nutsedge | Crab-grass | Barn-yard-grass | Wild Oats | Wheat | Corn | Soybean | Rice | Sorghum |
|---|---|---|---|---|---|---|---|---|---|---|---|---|---|
| Compound 5 | 0.4 | 2C, 5G, 6Y | 1C, 2G | 2C,8G | 5C,9G | 2C | 5G | 0 | 0 | 0 | 1C,5H | 2C,9G | 0 | 3C,6G |
| Compound 6 | 0.4 | 0 | 0 | 1C | 0 | 0 | 0 | 0 | 0 | 0 | 0 | 0 | 0 | 0 |

PRE-EMERGENCE

| Compound | Rate kg/ha | Morning-glory | Cocklebur | Cassia | Nutsedge | Crab-grass | Barn-yard-grass | Wild Oats | Wheat | Corn | Soybean | Rice | Sorghum |
|---|---|---|---|---|---|---|---|---|---|---|---|---|---|
| Compound 1 | 0.4 | 2C,9H | 9H | 7G | 10E | 2C,5G | 5C,9H | 2C,7G | 1C,7G | 2C,9H | 6H | 3C,8G | 5C,9H |
| Compound 2 | 0.4 | 9C | 4C,9H | 2C,7G | 2C,7G | 0 | 6C | 1C | 0 | 3C,8G | 3C,6H | 4C,7G | 1C,4G |

TABLE A-continued

| Compound | | | | | | | | | | | | | |
|---|---|---|---|---|---|---|---|---|---|---|---|---|---|
| Compound 3 (structure: O—SO₂—NH—C(=O)—NH- pyrimidine with 2,6-CH₃; benzofuran with gem-dimethyl) | 0.4 | 0 | 6G | 0 | 0 | 0 | 0 | 0 | 0 | 0 | 0 | 0 | 0 |
| Compound 4 (structure: O—SO₂—NH—C(=O)—NH- pyrimidine with 2,6-OCH₃; benzofuran with gem-dimethyl) | 0.4 | 2C | 9G | 2H | 2G | 0 | 2C,6H | 0 | 2C,8H | 0 | 3C,4H | 5C | 2C,9H |
| Compound 5 (structure: O—SO₂—NH—C(=O)—NH- pyrimidine with CH₃, OCH₃; benzofuran with gem-dimethyl) | 0.4 | 2H | 8G | 0 | 0 | 0 | 2C,2H | 0 | 2C,7G | 0 | 3C,3H | 4C | 2C,8H |
| Compound 6 (structure: O—SO₂—NH—C(=O)—NH- pyrimidine with 2,6-CH₃; benzofuran with gem-dimethyl) | 0.4 | 0 | 0 | 0 | 0 | 0 | 0 | 0 | 0 | 0 | 0 | 0 | 0 |

It is noted that compound No. 6 demonstrated no activity at the low rate used; it is thought it would demonstrate activity at higher rates.

Test B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (Cyperus rotundus), and several broadleaf weeds. The following grassy and broadleaf weeds were planted: crabgrass (Digitaria sanguinalis), barnyardgrass (Echinochloa crusgalli), wild oats (Avena fatua), johnsongrass (Sorghum halepense), dallisgrass (Paspalum dilatatum), giant foxtail (Setaria faberii), cheatgrass (Bromus secalinus), mustard (Brassica arvensis), cocklebur (Xanthium pensylvanicum), pigweed (Amaranthus retroflexus), morningglory (Ipomoea hederacea), cassia (Cassia tora), teaweed (Sida spinosa), velvetleaf (Abutilon theophrasti), and jimsonweed (Datura stramonium). A 12.5 cm diameter plastic pot was also filled with prepared soil and planted with rice and wheat. Another 12.5 cm pot was planted with sugarbeets. The above four containers were treated pre-emergence with one of the test compounds within the scope of the invention.

Twenty-eight days after treatment, the plants were evaluated and visually rated for response to the chemical treatments utilizing the rating system described previously for Test A. The data are summarized in Table B. Note that at low rates of application, the compound tested provided growth retardation of many weed species included in this test.

TABLE B

PRE-EMERGENCE ON FALLSINGTON SILT LOAM

|  | Compound 1 | | Compound 2 | |
| --- | --- | --- | --- | --- |
| Rate kg/ha | 0.06 | 0.25 | 0.06 | 0.25 |
| Crabgrass | 0 | 0 | 0 | 0 |
| Barnyardgrass | 3G | 5G | 0 | 0 |
| Sorghum | 3G | 4G,3H | 0 | 4G |
| Wild Oats | 3G | 3G | 0 | 0 |
| Johnsongrass | 5G | 7G,3H | 0 | 0 |
| Dallisgrass | 0 | 3G | 0 | 0 |
| Giant foxtail | 2G | 3G | 0 | 0 |
| Ky. bluegrass | 0 | 3G | 0 | 0 |
| Cheatgrass | 3G | 3G | 0 | 0 |
| Sugarbeets | 3G | 6G,3H | 0 | 0 |
| Corn | 0 | 3G | 0 | 3G |
| Mustard | 7G,3C | 8G,8C | 7G,5H | 8G,5C |
| Cocklebur | 0 | 3G | 0 | 5G |
| Pigweed | 8G,8C | 9G,9C | 0 | 0 |
| Nutsedge | 0 | 0 | 0 | 0 |
| Cotton | 2G | 4G | 0 | 0 |
| Morningglory | 3G | 4G | 0 | 0 |
| Cassia | 0 | 0 | 0 | 0 |
| Teaweed | 0 | 0 | 0 | 0 |
| Velvetleaf | 0 | 4G | 0 | 0 |
| Jimsonweed | 0 | 6G | 0 | 0 |
| Soybean | 0 | 3G | 0 | 0 |
| Rice | 3G | 3G | 0 | 0 |
| Wheat | 3G | 2G | 0 | 0 |

Test C

Two ten-inch in diameter plastic pans lined with polyethylene liners were filled with prepared Fallsington silt loam soil. One pan was planted with seeds of wheat (Triticum aestivum), barley (Hordeum vulgare), wild oats (Avena fatua), downy brome (Bromus tectorum), cheatgrass (Bromus secalinus), blackgrass (Alopecurus myosuroides), annual bluegrass (Poa annua), green foxtail (Setaria viridis), quackgrass (Agropyron repens), Italian ryegrass (Lolium multiflorum) and ripgut brome (Bromus rigidus). The other pan was planted with seeds of Russian thistle (Salsola kali), tansy mustard (Descuraina pinnata), smartweed (Polygonum pensylvanicum), tumble mustard (Sisymbrium altissium) kochia (Kochia scoparia), shepherd's purse (Capsella bursa-pastoris), Matricaria inodora, black nightshade (Solanum nigrum), yellow rocket (Barbarea vulgaris), wild mustard (Brassica kaber) and wild buckwheat (Polygonum convolvulus). The above two pans were treated pre-emergence. At the same time two pans in which the above plant species were growing were treated post-emergence. Plant height at the time of treatment ranged from 1–15 cm depending on plant species.

The compounds applied were diluted with a non-phytotoxic solvent and sprayed over-the-top of the pans. An untreated control and a solvent alone control were included for comparison. All treatments were maintained in the greenhouse for 20 days at which time the treatments were compared to the controls and the effects visually rated. The recorded data are presented in Table C.

TABLE C

|  | Compound 1 | | | |
| --- | --- | --- | --- | --- |
|  | Pre-Emergence | | Post-Emergence | |
| Rate kg/ha | 0.25 | 1.0 | 0.25 | 1.0 |
| wheat | 0 | 1C,2G | 1G | 1C,4G |
| barley | 0 | 3G | 3G | 1C,4G |
| wild oats | 0 | 4G | 1G | 3G |
| downy brome | 2G | 7G | 6G | 8G |
| cheatgrass | 3C,8G | 10E | 7G | 8G |
| blackgrass | 4C,8G | 10C | 1C,4G | 1C,7G |
| annual bluegrass | 2C,5G | 4C,8G | 4G | 2G |
| green foxtail | 1C,1G | 2C,3G | 3G | 5G |
| quackgrass | 3G | 8G | 1G | 5G |
| Italian ryegrass | 2G | 4G | 2G | 5G |
| ripgut brome | 3C,5G | 2C,8G | 5G | 7G |
| Russian thistle | 0 | 0 | 0 | 4G |
| tansy mustard | 10C | 10C | 10C | 10C |
| smartweed | — | — | — | — |
| tumble mustard | 9C,9G | 10C | 10C | 10C |
| kochia | 3G | 7G | 3G | 4G |
| shepherd's purse | 10C | 10C | 10C | 10C |
| Matricaria inodora | 9C,9G | 10C | 10C | 10C |
| black nightshade | 5C,7G | 9G | 6G | 1C,6G |
| yellow rocket | 9C,9G | 10C | 10C | 10C |
| wild mustard | 10C | 10C | 10C | 10C |
| wild buckwheat | 2C,3G | 3C,6G | 7C,8G | 7C,8G |

What is claimed is:
1. A compound of the formula:

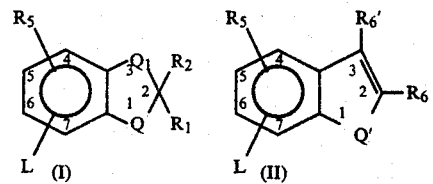

wherein
Q is O, S or SO$_2$;
Q$_1$ is CR$_3$R$_4$ or O;
L is OSO$_2$NHCONHA;
R$_1$ is H or C$_1$-C$_3$ alkyl;
R$_2$ is H or CH$_3$;
R$_3$ is H or CH$_3$;
R$_4$ is H or CH$_3$;

$R_5$ is H, $CH_3$, $OCH_3$, Cl, Br, $NO_2$, $CO_2R_7$, $SO_2R_8$, $OSO_2R_9$ or $SO_2NR_{10}R_{11}$;

$R_6$ is H or $C_1$-$C_3$ alkyl;

$R_6'$ is H or $CH_3$;

$R_7$ is $C_1$-$C_3$ alkyl, $CH_2CH=CH_2$, $CH_2CH_2OCH_3$ or $CH_2CH_2Cl$;

$R_8$ is $C_1$-$C_3$ alkyl;

$R_9$ is $C_1$-$C_3$ alkyl or $CF_3$;

$R_{10}$ and $R_{11}$ are independently $C_1$-$C_2$ alkyl;

A is

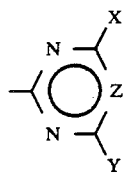

X is $CH_3$ or $OCH_3$;

Y is Cl, $CH_3$, $OCH_3$, $OC_2H_5$, $CH_2OCH_3$, $NH_2$, $NHCH_3$, $N(CH_3)_2$, $CH(OCH_3)_2$ or

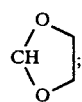

and

Z is CH;

provided that (1) L is fixed at the 4- or 7-position; and when L is at the 4-position, then $R_5$ is at the 5-position, and when L is at the 7-position, then $R_5$ is at the 6-position;

(2) in Formulae I and II, when Q is O and L is in the 4-position, and $R_5$ is other than H, then $R_1$ and $R_6$ are other than H;

(3) in Formula II, when Q is O and L is in the 7-position, and $R_5$ is other than H, then $R_6$ and $R_6'$ are other than H;

(4) in Formula II, when Q is S or $SO_2$ and $R_5$ is other than H, Br or $NO_2$, then $R_6$ and $R_6'$ are other than H;

(5) in Formula I, when Q is S, then $R_5$ is other than $SO_2R_8$;

(6) when $Q_1$ is O, then Q is O and $R_5$ is H; and (7) the total number of carbon atoms in $R_1$ to $R_4$ are less than or equal to 4.

2. Compounds of claim 1 where X is $OCH_3$ and $Q_1$ is O or $CH_2$.

3. Compounds of claim 2 where $R_5$ is H, Cl, $CH_3$ or $CO_2R_7$.

4. Compounds of claim 3 which have the structure shown in Formula I and where L is in the 7-position.

5. Compounds of claim 4 where $R_5$ is H.

6. Compounds of claim 5 where Q is O.

7. Compounds of claim 5 where Q is S or $SO_2$.

8. Compounds of claim 6 where Y is $CH_3$, $OCH_3$, $OC_2H_5$ or $CH_2OCH_3$ and $R_1$ and $R_2$ are independently H or $CH_3$.

9. Compounds of claim 7 where Y is $CH_3$, $OCH_3$, $OC_2H_5$ or $CH_2OCH_3$ and $R_1$ and $R_2$ are independently H or $CH_3$.

10. The compound of claim 1, N-[(4,6-dimethoxypyrimidin-2-yl)aminocarbonyl]sulfamic acid, 2,3-dihydro-2,2-dimethylbenzofuran-7-yl ester.

11. The compound of claim 1, N-[(4-methyl-6-methoxypyrimidin-2-yl)aminocarbonyl]sulfamic acid, 2,3-dihydro-2,2-dimethylbenzofuran-7-yl ester.

12. A composition suitable for controlling the growth of undesired vegetation which comprises an effective amount of a compound of any of claims 1 to 11 and at least one of the following: surfactant, solid or liquid diluent.

13. A method for controlling the growth of undesired vegetation which comprises applying to the locus to be protected an effective amount of a compound of any of claims 1 to 11.

* * * * *